United States Patent [19]
Kirschner et al.

[11] Patent Number: 6,066,460
[45] Date of Patent: May 23, 2000

[54] METHOD FOR CLONING SECRETED PROTEINS

[75] Inventors: Marc W. Kirschner, Newton, Mass.; Noriyuki Kinoshita, Hino, Japan

[73] Assignee: President and Fellows of Harvard College, Cambridge, Mass.

[21] Appl. No.: 09/121,920

[22] Filed: Jul. 24, 1998

Related U.S. Application Data

[60] Provisional application No. 60/053,586, Jul. 24, 1997.

[51] Int. Cl.$^7$ .............................. C12Q 1/68; C12P 19/34; C12N 15/11; C07H 21/00
[52] U.S. Cl. .............................. 435/6; 435/91.1; 536/23.1
[58] Field of Search .................... 435/6, 91.1; 536/23.1, 536/23.5

[56] References Cited

U.S. PATENT DOCUMENTS

| | | | |
|---|---|---|---|
| 4,983,521 | 1/1991 | Lingappa et al. | 435/69.1 |
| 5,492,817 | 2/1996 | Thompson et al. | 435/68.1 |
| 5,536,637 | 7/1996 | Jacobs | 435/6 |
| 5,589,372 | 12/1996 | Robinson | 435/193 |
| 5,643,722 | 7/1997 | Rothschild et al. | 435/6 |

FOREIGN PATENT DOCUMENTS

| | | |
|---|---|---|
| 217 239 A1 | 1/1985 | Germany . |
| WO 91/05058 | 4/1991 | WIPO . |
| WO 96/40904 | 12/1996 | WIPO . |
| WO 98/25959 | 6/1998 | WIPO . |

OTHER PUBLICATIONS

Aaij, et al., "A Study of Minor RNA Components of Rat–Liver Microsomes," *Biochemica et Biophysica Acta*, 246, pp. 233–238 (1971).

Cupello, et al, "Poly(A) Associated RNA from Mitochondria and Microsomes of Rat Brain," *Experientia*, 32/7 pp. 872–874, (1976).

Dingman, et al., "Rat Liver Cytoplasmic Ribonucleic Acids: Some Aspects of their Localization and Isolation," *Biochemica et Biophysica Acta*, 224, pp. 114–127 (1970).

Harrison et al., "Preparation of Immunoglobin Light–Chain MRNA from Microsomes without the Use of Detergent," *Eur. J. Biochem.*, 47, pp. 621–627 (1974).

Lust et al., "Conditions of Phenol Extraction of RNA from Rat Liver Subcellular Cytoplasmic Fractions," *Preparative Biochemistry*, 2(s), pp. 113–124 (1972).

Merrick, et al., "Assays for Eukaryotic Translation Factors that Bind mRNA," *Methods: A Companion to Methods in Enzymology* 11, pp. 333–342, Article No. ME960431 (1997).

Munns, et al, "Rapidly Labelled Ribosomal RNA from the Agranular Microsomal Membranes of Rat Liver," *Archives of Biochemistry and Biophysics* 127, pp. 419–425 (1968).

Schneider et al., "The Association of Deoxyribonucleic Acid with Liver Microsomes," *The Journal of Biological Chemistry*, vol. 244, No. 18, pp. 4843–4851, Sep. 25, 1969.

Siegel et al, "Elongation Arrest is not a Prerequisite for Secretory Protein Translocation Across the Microsomal Membrane," *The Journal of Cell Biology*, vol. 100, pp. 1913–1921, Jun. 1985.

Storb, Ursula, "Quantitation of Immunoglobulin Genes by Nucleic Acid Hybridization with RNA from Myeloma and Spleen Microsomes," *The Journal of Immunology*, vol. 108, No. 3, Mar. 1972.

Tacchini, L., et al, "Ferritin mRNAs on Rat Liver Membrane–bound Polysomes Synthesize Ferritin that does not Translocate across Membranes," *Biochimica et Biophysica Acta*, 1131, pp. 133–138, 1992.

White, J., et al, Properties of Rat Brain Microsomal Ribonucleic Acid Containing Polyadenylate, *Biochemical Society Transactions*, 553$^{rd}$ Meeting, London, vol. 3, pp. 94–95, (1975).

Klein, R. et al., "Selection for genes encoding secreted proteins and receptors", *Proc. Natl. Acad. Aci. USA*, 93:7108–7113 (1996).

Adesnik et al. (1981) Segregation of specific classes of messenger RNA into free and membrane–bound polysomes. *Eur. J. Biochem.* 114:271–284, Jul. 1981.

*Primary Examiner*—Robert A. Schwartzman
*Attorney, Agent, or Firm*—Foley, Hoag & Eliot, LLP; Matthew P. Vincent; Isabelle M. Clauss

[57] ABSTRACT

The invention provides a method for isolating nucleic acids encoding proteins comprising a signal peptide, e.g., a secreted protein. The method of the invention comprises isolating an RNA molecule associated with an endoplasmic reticulumn membrane preparation under conditions wherein the RNA is at least partially translated. The invention also provides a library of nucleic acids encoding proteins comprising a signal peptide, individual nucleic acids isolated according to the method of the invention, peptides encoded thereby, pharmaceutical compositions comprising such and kits for performing the method of the invention.

34 Claims, 4 Drawing Sheets

SEQUENCE LISTING

<160> NUMBER OF SEQ ID NOS: 27

<210> SEQ ID NO 1
<211> LENGTH: 21
<212> TYPE: DNA
<213> ORGANISM: primer

<400> SEQUENCE: 1
acctccccct gaacctgaaa c                                    21

<210> SEQ ID NO 2
<211> LENGTH: 18
<212> TYPE: DNA
<213> ORGANISM: primer

<400> SEQUENCE: 2
atgcttgaca ttatggtg                                        18

<210> SEQ ID NO 3
<211> LENGTH: 18
<212> TYPE: DNA
<213> ORGANISM: primer

<400> SEQUENCE: 3
ttatctcata gcagggag                                        18

<210> SEQ ID NO 4
<211> LENGTH: 18
<212> TYPE: DNA
<213> ORGANISM: primer

<400> SEQUENCE: 4
aatggatttc agagacca                                        18

<210> SEQ ID NO 5
<211> LENGTH: 18
<212> TYPE: DNA
<213> ORGANISM: primer

<400> SEQUENCE: 5
ccaaggctaa agttgcag                                        18

<210> SEQ ID NO 6
<211> LENGTH: 21
<212> TYPE: DNA
<213> ORGANISM: primer

<400> SEQUENCE: 6
tcctccagac cagaccttcc a                                    21

<210> SEQ ID NO 7
<211> LENGTH: 21
<212> TYPE: DNA
<213> ORGANISM: primer

<400> SEQUENCE: 7
cgtattagtt cgtttgtttg t                                    21

<210> SEQ ID NO 8
<211> LENGTH: 21

```
<212> TYPE: DNA
<213> ORGANISM: primer

<400> SEQUENCE: 8
gtgcctgccg ctttctttcc a                                              21

<210> SEQ ID NO 9
<211> LENGTH: 21
<212> TYPE: DNA
<213> ORGANISM: primer

<400> SEQUENCE: 9
aactcacgac tccaacttcc a                                              21

<210> SEQ ID NO 10
<211> LENGTH: 21
<212> TYPE: DNA
<213> ORGANISM: primer

<400> SEQUENCE: 10
agccctgccg tagtatgtgt g                                              21

<210> SEQ ID NO 11
<211> LENGTH: 21
<212> TYPE: DNA
<213> ORGANISM: primer

<400> SEQUENCE: 11
ctgtgggtct ggtccgtatc a                                              21

<210> SEQ ID NO 12
<211> LENGTH: 21
<212> TYPE: DNA
<213> ORGANISM: primer

<400> SEQUENCE: 12
agatgatgac tgtgcccttg a                                              21

<210> SEQ ID NO 13
<211> LENGTH: 21
<212> TYPE: DNA
<213> ORGANISM: primer

<400> SEQUENCE: 13
cctttcctcc tgtgcttggt g                                              21

<210> SEQ ID NO 14
<211> LENGTH: 18
<212> TYPE: DNA
<213> ORGANISM: primer

<400> SEQUENCE: 14
cagtgcagcg ctggaaag                                                  18

<210> SEQ ID NO 15
<211> LENGTH: 18
<212> TYPE: DNA
<213> ORGANISM: primer

<400> SEQUENCE: 15
tgcgttgcgg taattcac                                                  18
```

```
<210> SEQ ID NO 16
<211> LENGTH: 21
<212> TYPE: DNA
<213> ORGANISM: primer

<400> SEQUENCE: 16
ttctcgccgt tcttttgata a                                              21

<210> SEQ ID NO 17
<211> LENGTH: 21
<212> TYPE: DNA
<213> ORGANISM: primer

<400> SEQUENCE: 17
acacgtgcat tcctctacca t                                              21

<210> SEQ ID NO 18
<211> LENGTH: 17
<212> TYPE: DNA
<213> ORGANISM: primer

<400> SEQUENCE: 18
caccagaaca cagatac                                                   17

<210> SEQ ID NO 19
<211> LENGTH: 18
<212> TYPE: DNA
<213> ORGANISM: primer

<400> SEQUENCE: 19
caaccttccc atcaacca                                                  18

<210> SEQ ID NO 20
<211> LENGTH: 20
<212> TYPE: DNA
<213> ORGANISM: primer

<400> SEQUENCE: 20
cagattggtg ctggatatgc                                                20

<210> SEQ ID NO 21
<211> LENGTH: 20
<212> TYPE: DNA
<213> ORGANISM: primer

<400> SEQUENCE: 21
actgccttga tgactcctag                                                20

<210> SEQ ID NO 22
<211> LENGTH: 22
<212> TYPE: DNA
<213> ORGANISM: primer

<400> SEQUENCE: 22
agtccgatct cagtgaaggg ca                                             22

<210> SEQ ID NO 23
<211> LENGTH: 21
<212> TYPE: DNA
<213> ORGANISM: primer
```

-continued

```
<400> SEQUENCE: 23
tgtgtgtggc ctgagctgta g                                              21

<210> SEQ ID NO 24
<211> LENGTH: 18
<212> TYPE: DNA
<213> ORGANISM: primer

<400> SEQUENCE: 24
acaactggaa gcactgga                                                  18

<210> SEQ ID NO 25
<211> LENGTH: 18
<212> TYPE: DNA
<213> ORGANISM: primer

<400> SEQUENCE: 25
tcttattcca gaggaacc                                                  18

<210> SEQ ID NO 26
<211> LENGTH: 20
<212> TYPE: DNA
<213> ORGANISM: primer

<400> SEQUENCE: 26
caagagcgga gaaactgtgt                                                20

<210> SEQ ID NO 27
<211> LENGTH: 20
<212> TYPE: DNA
<213> ORGANISM: primer

<400> SEQUENCE: 27
gaaggagcaa caagaggaag                                                20
```

METHOD FOR CLONING SECRETED PROTEINS

This application claims the benefit of U.S. Provisional Application No. 60/053,586, filed Jul. 24, 1997.

STATEMENT OF RIGHTS

This invention was made in the course of work supported by the U.S. Government. The U.S. Government therefore has certain rights in the invention.

BACKGROUND OF THE INVENTION

Many biologically important molecules, in particular for use in therapy, are secreted proteins. For example, growth factors, interferons, erythropoietin, and insulin have been used successfully for treating various conditions and diseases.

Secreted proteins are characterized by the presence of a hydrophobic signal peptide at the amino terminus of the protein. The hydrophobic signal sequence is typically from about 16 to about 30 amino acids long and contains one or more positively charged amino acid residues near its N-terminus, followed by a continuous stretch of 6–12 hydrophobic residues. Signal peptides from various secreted proteins have otherwise no sequence homology. The presence of a hydrophobic signal peptide at the amino terminus of a protein mediates its association with the rough endoplasmic reticulumn (ER), which in turn mediates its secretion from the cell.

The mechanism by which peptides or proteins having a signal peptide associate with the endoplasmic reticulumn and are secreted is as follows. Protein synthesis begins on free ribosomes. When the elongating peptide is about 70 amino acids long, the signal peptide is recognized by a particle, termed a "signal recognition particle" or "SRP", which in turn is capable of interacting with a receptor, termed "SRP receptor", located on the ER. Thus, growing peptides having a signal peptide are targeted to the ER, where peptide synthesis continues on the rough ER. At some point during the protein synthesis or after the protein synthesis is completed, the protein is translocated across the ER membrane into the ER lumen, where the signal peptide is cleaved off. There the protein can be postranslationally modified, e.g., glycosylated. Whether posttranslationally modified or not, the protein can then be directed to the appropriate cellular compartment, e.g., secreted outside the cell.

Several systems have recently been developed to isolate nucleic acids encoding secreted proteins. One system which is used frequently and of which several variations exist is a system termed "Sequence Signal Trap". One such system (such as the Genetic Institute's DiscoverEase™ program) is yeast based and uses the yeast invertase gene, which cleaves the disaccharide sucrose into monosaccharides glucose and fructose. According to the system, a library of cDNAs is cloned upstream of the gene encoding invertase and yeast cells are selected on sucrose. Since yeast cells cannot ingest sucrose, but can ingest fructose and glucose, only yeasts secreting invertase are able to grow on sucrose. Thus, only yeasts which contain a cDNA containing a signal sequence properly fused to the invertase gene will permit invertase to be secreted and will survive on sucrose.

However, such systems have several drawbacks. For example, the sequence signal trap system requires that the sequence signal be fused properly, e.g., in frame, to the gene encoding the invertase. Even where the signal sequence is in frame, this may produce a fusion protein, which may be instable. Thus, only a fraction of the cDNAs containing a signal sequence will be fused properly to the invertase gene to permit secretion of the invertase gene. Furthermore, this system requires that the protein containing the signal sequence be secreted. However, it is known that numerous proteins containing signal peptides are trapped in the endoplasmic reticulumn. Accordingly, the requirement that the fusion protein containing the signal peptide be actually secreted further reduces the efficiency of cloning secreted proteins.

Thus, it is highly desirable to have a system for isolating nucleic acids encoding secreted proteins which is more efficient and reliable than the existing sequence signal trap systems.

SUMMARY OF THE INVENTION

The invention pertains to a method for isolation of nucleic acids encoding proteins comprising a signal peptide, e.g., secreted proteins. In a preferred embodiment, the invention comprises isolating an RNA molecule associated with microsomes. An even more preferred method is outlined in FIG. 1. The method of the invention provides several advantages over known methods for cloning genes encoding secreted proteins. In particular, the method of the invention does not involve a fusion protein. Rather, the method selects natural secreted proteins. Furthermore, the method of the invention does not require the protein to be secreted.

The invention is based at least in part on the observation that nucleic acid molecules encoding secreted proteins can be cloned from RNA that is isolated from microsomes. As shown herein, an RNA molecule encoding a protein having a signal peptide can be isolated from a population of RNA molecules by in vitro translation of a population of RNA molecules, contacting the RNA molecules being translated with microsomes, purification of the microsomes from the free ribosomes, and isolation of RNA from the purified microsomes.

Accordingly, the invention provides a method for isolating a nucleic acid encoding a protein having a signal peptide, such as a secreted protein. The method comprises isolating an RNA molecule associated with microsomes under conditions wherein the RNA is at least partially translated. In a preferred embodiment, the method further comprises synthesizing a single stranded DNA molecule from the RNA molecule. The single stranded DNA molecule can further be converted into a double stranded DNA molecule. The RNA, single stranded or double stranded DNA molecule can be inserted in a vector, such as an expression vector. In one embodiment, the method further comprises producing a protein from the expression vector. The RNA, DNA, or protein can be used for preparing a pharmaceutical composition comprising a pharmaceutically acceptable carrier.

In one embodiment of the invention, the microsomes and the RNA are from the same cell, such as a mammalian cells, e.g., a human cell. In another embodiment, the microsomes and the RNA are heterologous.

In one instance, the RNA which is at least partially translated is an RNA which is translated in an in vitro translation system, such as a reticulocyte lysate. The RNA can be isolated from a cell or tissue sample, e.g., a human cell or tissue. However, the RNA can also be transcribed in vivo, i.e., the RNA that is at least partially translated is obtained from a cell.

In a preferred embodiment of the invention, RNA, an in vitro translation system and microsomes are contacted, to thereby produce RNA which is partially translated and wherein RNA encoding a protein comprising a signal peptide is associated with the microsomes. In an even preferred embodiment, the method further comprises isolating the microsomes and the RNA associated therewith, such as by sucrose density gradient centrifugation.

The invention also provides a method for enriching a population of RNA molecules in RNA molecules encoding a protein comprising a signal peptide, comprising (i) contacting the population of RNA molecules with a translation system, to thereby produce at least partially translated RNA molecules; (ii) contacting the at least partially translated RNA molecules with microsomes under conditions in which the partially translated RNA molecules comprising a signal peptide associate with the microsomes; (iii) isolating the microsomes and the RNA molecules associated with the microsomes; and (iv) isolating the RNA molecules from the microsomes, to thereby produce a population of RNA molecules enriched in RNA molecules encoding a protein comprising a signal peptide. The enrichment of the RNA population in RNA molecules containing a signal sequence can be of a factor of about 10, preferably at least about 100, at least about $10^3$, at least about $10^4$, at least about $10^5$, at least about $10^6$, at least about $10^7$ or at least about $10^8$.

Also within the scope of the invention are libraries of nucleic acids encoding proteins comprising a signal peptide, prepared according to a method of the invention. The library can be a cDNA library or an expression library.

The invention further provides nucleic acids, such as nucleic acids encoding secreted proteins, isolated according to the method of the invention and peptides encoded thereby. Nucleic acids and peptides of the invention can be prepared as a pharmaceutical preparation comprising a pharmaceutically acceptable carrier.

Other features and advantages of the invention will be apparent from the following detailed description and claims.

DETAILED DESCRIPTION OF THE INVENTION

Figure 1:
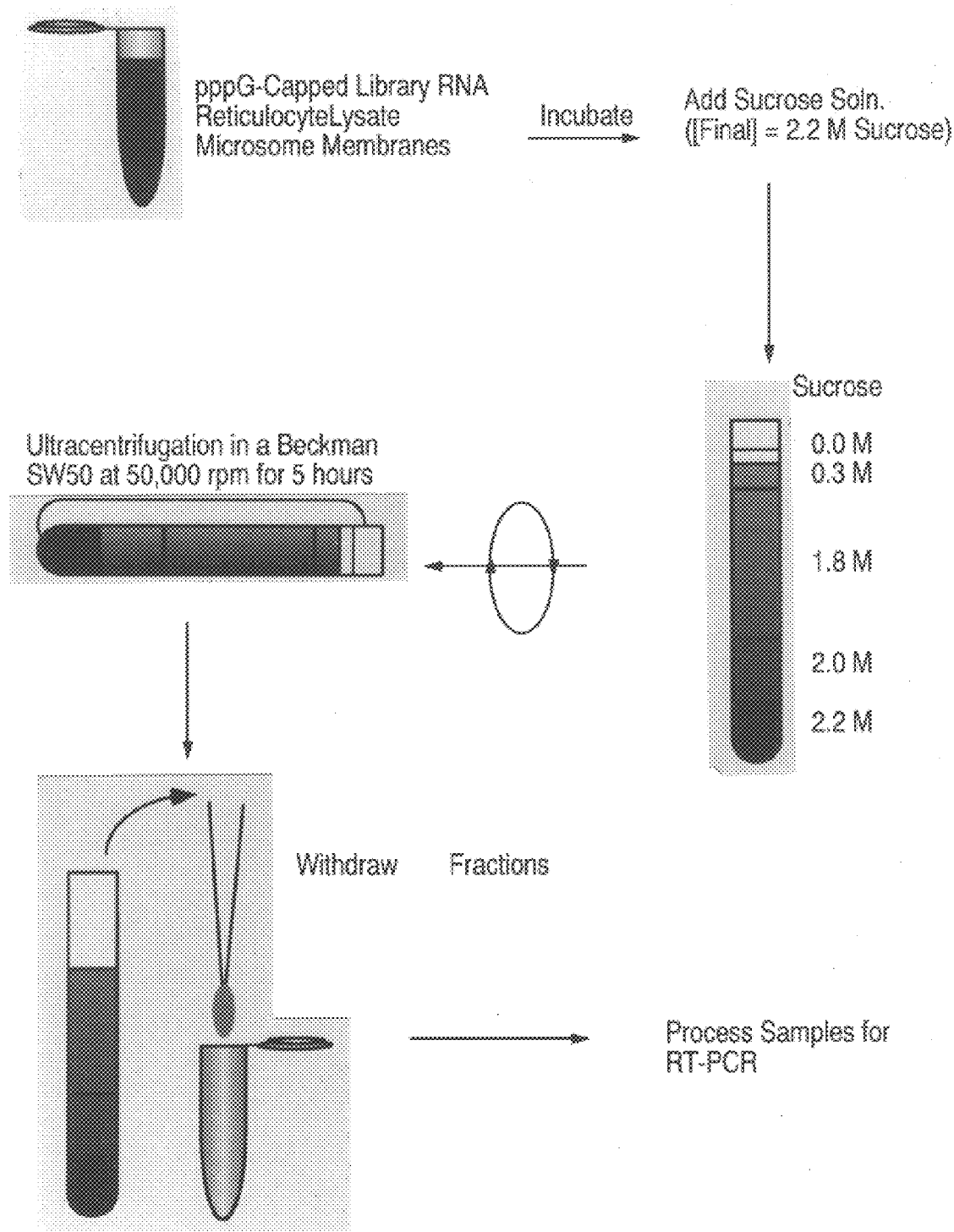
FIG. 1 outlines the steps of a preferred method of the invention for isolating RNA molecules encoding proteins containing a signal peptide.

The endoplasmic reticulum (ER) of eukaryotic cells provides the cells with a mechanism for separating newly synthesized molecules that belong to the cytoplasm from those that do not. Lipids, proteins and complex carbohydrates destined for transportation to the Golgi apparatus, to the plasma membrane, to lysosomes, or to the cell exterior are all synthesized in association with the ER. Association of proteins with rough ER is mediated through the presence of a hydrophobic signal peptide at the amino terminus of the protein.

The ER has two functionally and structurally distinct regions: the rough endoplasmic reticulumn, which is covered with ribosomes on the cytoplasmic side of the membrane and the smooth endoplasmic reticulumn, which lacks ribosomes. The rough endoplasmic ribosome is involved in the synthesis of secretory proteins, integral, ER, Golgi, and plasma-membrane proteins, glycoproteins and lysosome proteins. Though all nucleated cells, except sperm cells, have ER, the amount of rough ER varies from one cell type to another, depending of the function of the cell. For example, a cell specialized in protein secretion, such as a pancreatic acinar cell and antibody secreting plasma cell, or a cell undergoing extensive membrane synthesis, e.g., an immature egg or a retinal rod cell, are particularly rich in rough ER. The smooth ER is not involved in protein synthesis.

Upon disruption of a tissue or cells by homogenization, the ER is fragmented into many smaller (about 100 nm diameter) closed vesicles called "microsomes", which are relatively easy to purify. Microsomes derived from the rough ER, are covered with ribosomes on the outside of the microsome and are termed "rough microsomes". Such a tissue or cell homogenate also contains many vesicles of a size similar to the rough microsomes, but which do not contain ribosomes on their surface. Such smooth microsomes are derived in part from the smooth portions of the ER and in part from vesiculated fragments of plasma membranes, Golgi apparatus, and mitochondria. Rough microsomes can be separated from smooth microsomes, e.g., by sucrose gradient centrifugation. In fact, smooth microsomes have a low density and stop sedimenting and float at a low sucrose concentration, whereas rough microsomes have a high density and stop sedimenting and float at high sucrose concentration.

The present invention provides a method and reagents for isolating a nucleic acid encoding a protein having a signal peptide, by isolating an RNA molecule from microsomes or other ER preparation. In a preferred embodiment, the protein having a signal peptide is a secreted protein. The protein can also be an integral, ER, Golgi, plasma-membrane protein, a glycoprotein, or a lysosome protein. In another embodiment, a population of RNA molecules is isolated from microsomes and used to prepare a library of nucleic acids encoding proteins having a signal peptide. In a preferred embodiment of the invention, the library is a cDNA library. In yet another embodiment, the invention further comprises isolating individual members of the library, e.g., cDNAs encoding secreted proteins.

In an exemplary embodiment of the invention, the RNA molecule or the population of RNA molecules isolated from microsomes and the microsomes are heterologous, i.e., originate from different sources. For example, a population of RNA molecules being translated can first be contacted with heterologous microsomes and one or more RNA molecule associating with the microsomes can be isolated. In one embodiment, the RNA is first incubated with an in vitro transcription system and then microsomes are added to the in vitro transcription reaction. Alternatively, the RNA is added to a mixture containing an in vitro translation system and microsomes.

Definitions

For convenience, the meaning of certain terms and phrases employed in the specification, examples, and appended claims are provided below.

The phrase "at least partially translated RNA molecule" refers to an RNA molecule which is associated with at least one ribosome and which has served as a template for the synthesis of a peptide of sufficient length to be capable of associating with the endoplasmic reticulum (ER), e.g., by interaction with SRP receptors or by being inserted into the ER membrane. Accordingly, a partially translated RNA molecule will have been translated into a polypeptide of at least about 50 amino acids, preferably at least about 60 amino acids, at least about 70 amino acids, at least about 80 amino acids, at least about 90 amino acids or at least about 100 amino acids. In fact, the N-terminal signal sequence emerges from the ribosome only when the polypeptide is about 70 amino acids long, since about 30 amino acids remain buried in the ribosome (James Darnell, Harvey Lodish, and David Baltimore, *Molecular Cell Biology* (1990) Scientific American Books). In a preferred embodiment, the at least partially translated RNA molecule is not completely translated, since in this case the ribosome/RNA/polypeptide complex dissociates from the ER membrane.

The phrase "converting a single stranded DNA molecule into a double stranded DNA molecule" refers to any molecular process whereby a single stranded DNA molecule is rendered double stranded. Such a molecular process can be, e.g., primer extension from a primer hybridizing to the single stranded DNA molecule.

The term "in vitro translation system", which is used herein interchangeably with the term "cell-free translation system" refers to a translation system which is a cell-free extract containing at least the minimum elements necessary for translation of an RNA molecule into a protein. An in vitro translation system typically comprises at least ribosomes, tRNAs, initiator methionyl-tRNA$^{Met}$, proteins or complexes involved in translation, e.g., eIF$_2$, eIF$_3$, the cap-binding (CB) complex, comprising the cap-binding protein (CBP) and eukaryotic initiation factor 4F (eIF$_{4F}$).

The term "isolated" as used herein with respect to nucleic acids, such as DNA or RNA, refers to molecules separated from other DNAs or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "heterologous" when referring to ER preparations, such as microsomes, and RNA means that the ER preparations and the RNA are not from the same cell, i.e., that the ER preparations are from one source of cells and the RNA is RNA isolated from a second source or is synthesized in vitro. The ER preparations and the RNA can be heterologous with respect to each other if they originate from the same cell or tissue, so long as the RNA and the ER preparations have been separated (enriched separately from one another) prior to being contacted.

As used herein, the term "microsome" refers to a rough microsome, as opposed to a smooth microsome. Accordingly, a "microsome" contains SRP receptors which are capable of interacting with an SRP complex which itself interacts with a signal peptide.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides.

The term "operably linked" is intended to mean that the promoter is associated with the nucleic acid in such a manner as to facilitate transcription of the nucleic acid from the promoter.

The terms "protein", "polypeptide" and "peptide" are used interchangeably herein when referring to the translation product of a nucleic acid (e.g. a gene product).

The term "RNA" refers to a nucleic acid in which the sugar is ribose, as opposed to deoxyribose in DNA. RNA is intended to include any nucleic acid which can be entrapped by ribosomes and translated into protein.

The term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

The term "secreted protein" refers to a protein having at least a portion which is extracellular and includes proteins which are completely extracellular (i.e., not attached to a cell) and proteins which are cytoplasmic membrane proteins. The cell can be a prokaryotic cell, e.g., bacterial cell or the cell can be a eukaryotic cell.

The term "signal peptide" refers to a stretch of amino acids mediating the attachment of a protein to the ER, such that the protein having a signal peptide is secreted or inserted into a cell membrane.

The term "signal sequence" refers to a nucleotide sequence encoding a signal peptide.

The term "soluble protein" refers to a secreted protein which is completely extracellular and which are not embedded in a cell membrane.

As used herein, the term "transfection" means the introduction of a nucleic acid, e.g., an expression vector, into a recipient cell by nucleic acid-mediated gene transfer. The term "transduction" is generally used herein when the transfection with a nucleic acid is by viral delivery of the nucleic acid. "Transformation", as used herein, refers to a process in which a cell's genotype is changed as a result of the cellular uptake of exogenous DNA or RNA, and, for example, the transformed cell expresses a recombinant form of a polypeptide or, in the case of anti-sense expression from the transferred gene, the expression of a naturally-occurring form of the recombinant protein is disrupted.

The term "translation system" refers to a cellular or cell-free translation system. The term "cellular translation system" refers to a translation system which is a permeabilized cell, as opposed to a "cell-free translation system", which refers to a cell extract or a reconstituted translation system. The term "reconstituted translation system" refers to a system consisting of purified translation factors, such as elongation factors.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

Exemplary Sources of, and Methods of Obtaining, RNA

In a preferred embodiment, a population of RNA molecules (RNA) is contacted with an in vitro translation system together, before, or after incubation with microsomes. The population of RNA molecules can be from a cell or a tissue. In a preferred embodiment, the RNA is from a eukaryote. In an even more preferred embodiment, the RNA is from a vertebrate, e.g., a mammal. In a yet even more preferred embodiment, the RNA is from a human.

Preferred cells and tissues from which RNA can be extracted for use in the method of the invention include RNA from tissues which are known to secrete numerous proteins, e.g., exocrine or endocrine tissues. Preferred tissues include glands, exocrine glands, e.g., pancreas, salivary glands, submandibular gland, and others. Other preferred tissues include endocrine tissues, e.g., thyroid.

RNA can be extracted from cells or tissues according to methods known in the art. In a preferred embodiment, RNA can be extracted from monolayers of mammalian cells grown in tissue culture, cells in suspension or from mammalilan tissue that can readily be dispersed in single cells. RNA can be extracted from such sources by, e.g.,treating the cells with proteinase K in the presence of SDS. In another embodiment, RNA is extracted by organic solvents. In yet another embodiment, RNA is extracted by differential precipitation to separate high molecular weight RNA from other nucleic acids. RNA can also be extracted from a specific cellular compartment, e.g., nucleus or the cytoplasm. In such methods, the nucleus is either isolated for purification of RNA therefrom, or the nucleus is discarded for purification of cytoplasmic RNA. Further details regarding these and other RNA extraction protocols are set forth, e.g., in Molecular Cloning A Laboratory Manual, 2nd Ed., ed. by Sambrook, Fritsch and Maniatis (Cold Spring Harbor Laboratory Press: 1989).

For instance, RNA can be extracted by a method using guanidium thiocyanate and purification of the RNA on a cesium chloride gradient. Accordingly, tissue or cells are lysed in the presence of guanidium thiocyanate and the cell lysate is loaded on a cushion of cesium chloride (CsCl) and centrifuged at high speed, such that the RNA is recovered in the pellet and the DNA is left in the supernatant after the centrifugation. The RNA can then be recovered by ethanol precipitation. This method is set forth in details, e.g., in Molecular Cloning A Laboratory Manual, 2nd Ed., ed. by Sambrook, Fritsch and Maniatis (Cold Spring Harbor Laboratory Press: 1989).

In order to prevent RNA from being degraded by nucleases, e.g., by RNAases, that may be present, the extraction of RNA, and reactions involving RNA are performed in "RNAase free conditions". Various methods known in the art can be used to maintain RNAase free conditions. For example, during RNA extraction, potent denaturing agents, such as guanidium hydrochloride and guanidium thiocyanate can be used to denature and thereby inactivate nucleases. Reducing agents, e.g., β-mercaptoethanol, can also be used to inactivate ribonucleases. This combination of agents is particularly useful when isolating RNA from tissues rich in ribonucleases, e.g., pancreas (Chirgwin et al. (1979) Biochemistry 18:5294).

Other reagents that can be added to a solution containing RNA to prevent degradation of the RNA include RNAase inhibitors, also referred to herein as "protein inhibitor of RNAases", e.g., RNasin® which can be obtained, from Promega Corp. (Madison, Wis.) (e.g., Cat #N2514). Protein inhibitors of RNAases are preferably not included during extraction of RNA using potent denaturing agents (since these will also denature the protein inhibitor of RNAases). However, it is preferable to include such protein inhibitors of RNAases during RNA extraction using more gentle methods of cell lysis and RNAse inhibitors are preferably present at all stages during the subsequent purification of RNA.

Yet another reagent that can be added to a solution containing RNA to prevent degradation of the RNA include vanadyl-ribonucleoside complexes. The complexes formed between the oxovanadium IV ion and any of the four ribonucleosides are transition-state analogs that bind to many RNAases and inhibit their activity almost completely. The four vanadyl-ribonucleoside complexes are preferably added to intact cells and preferably used at a concentration of 10 mM during all stages or RNA extraction and purification. Yet in another embodiment, macaloid is used to absorb RNAases.

Prior to contacting the RNA with a translation system and microsomes, the RNA can be partially purified. For example, the polyA$^+$RNA can be isolated from total RNA by, e.g., oligodT affinity chromatography, according to methods known in the art. Use of polyA$^+$RNA relative to total RNA may improve the translation efficiency in certain situations.

In another embodiment, RNA or polyA$^+$RNA having a specific molecular size can be isolated. Thus, if one desires to isolate an RNA molecule encoding a small secreted protein, RNA molecules of small sizes can be isolated and incubated with a translation system and microsomes. For example, RNA of sizes of about or less than 1 kb, about 2 kb, about 3 kb, about 4 kb, about 5 kb, about 6 kb, about 7 kb, about 8 kb, about 8 kb, about 9 kb or at least about 10 kb can be selected. RNA having a size between about 1 and 3 kb, between about 3 and 5 kb, or between about 5 and 10 kb can also be isolated. Size fractionation of RNA can be performed, e.g., by electrophoresis through agarose gels. After the electrophoresis, the gels can be stained, e.g., with ethidium bromide, to visualize the RNA, and RNA having the desired size can be recovered from the gel. Ribosomal RNA of known size can be used as molecular weight standards. Gel electrophoresis is preferably carried out in the presence of an RNAase inhibitor, e.g., methylmercuric hydroxide.

Another method that can be used to isolate RNA of a specific size is by centrifugation through a sucrose gradient, e.g., containing methylmercuric hydroxide. According to this method, an RNA solution is loaded onto a sucrose gradient (10–30% weight/volume) containing about 10 mM methylmercuric hydroxide and centrifuged, at 34,000rpm for about 15 hours. A gradient of RNA molecules, reflecting the size of the RNA molecules, will be formed in the tube after centrifugation. Fractions can then be collected and the RNA isolated, e.g., by ethanol precipitation.

In another embodiment, the source of RNA from which RNA molecules encoding proteins containing signal peptides are isolated, is obtained by in vitro transcription of template DNA. For example, the RNA can be synthesized in vitro from a DNA library, e.g., cDNA library. Alternatively, the RNA can be synthesized from another source of DNA, e.g., genomic DNA. In a preferred embodiment of the invention, the DNA to be in vitro transcribed is operably linked to, and is located downstream of, an RNA polymerase promoter, e.g., a bacteriophage promoter, such as SP6, T3 or T7 promoter. In one embodiment, the DNA to be transcribed is cloned in a cDNA library at a site located downstream of a bacteriophage promoter and transcription is carried out from the library itself, resulting in a library of RNA molecules. If the DNA to be transcribed is in a vector which does not contain a bacteriophage promoter, the cDNA inserts can first be excised from the vector and cloned in another vector from which the inserts can be in vitro transcribed.

Many vectors for in vitro transcription are available commercially. These may contain one or more of the promoters SP6, T3 and T7 and may additionally contain a polyA sequence at the 3' end of the polylinker in which the DNA of interest is inserted. A "polylinker" refers to a nucleotide sequence containing several restriction enzyme recognition sites. Examples of vectors include the series of SP6 vectors, e.g,. SP64 (Krieg and Melton, infra), BlueScript, and pCS2+. Vectors that can be used for in vitro transcription are also described, e.g., in U.S. Pat. No. 4,766,072.

An in vitro transcription reaction can be carried out according to methods well known in the art. Kits for performing in vitro transcription kits are also commercially available from several manufacturers. In an illustrative embodiment, an in vitro transcription reaction is carried out as follows. A vector containing an RNA Polymerase promoter and an insert of interest is preferably first linearized downstream of the insert, by e.g., restriction digest with an appropriate restriction enzyme. The linearized DNA is then incubated for about I hour at 37 or 40° C. (depending on the RNA polymerase) in the presence of ribonucleotides, an RNAase inhibitor, an RNA polymerase recognizing the promoter that is operably linked upstream of the insert to be transcribed, and an appropriate buffer containing Tris.Cl, $MgCl_2$, spermidine and NaCl. Following the transcription reaction, RNAase free DNAse can be added to remove the DNA template and the RNA can be purified by, e.g., a phenol-chlorophorm extraction. Usually about 5–10 $\mu$g of RNA can be obtained per microgram of template DNA. Further details regarding this protocol are set forth, e.g., in Molecular Cloning A Laboratory Manual, 2nd Ed., ed. by Sambrook, Fritsch and Maniatis (Cold Spring Harbor Laboratory Press: 1989).

In another embodiment, the RNA is "capped" prior to contacting it with an in vitro translation system. In certain situations, efficient translation of eukaryotic RNA requires that the 5' end of an RNA molecule is "capped", i.e., that the 5' nucleotide at the 5' end of the RNA has a 5'—5' linkage with a 7-methylguanylate ("7-methyl G") residue. The presence of a 7-methyl G on an RNA molecule in a 5'—5' linkage is referred to as a "cap". It has been proposed that recognition of the translational start site in mRNA by the eukaryotic ribosomes involves recognition of the cap, followed by binding to specific sequences surrounding the initiation codon on the RNA. Accordingly, it is possible that in certain embodiments of the invention, capping of the RNA extracted from a cell or tissue or synthesized in vitro prior to contacting the RNA with an in vitro translation system improves the translation efficiency of the RNA and thus the amount of RNA eventually recovered from the microsomes. Thus, in one embodiment, the RNA is contacted with methyl-7 (5')PPP(5')guanylate (available, e.g., from Boehringer Mannheim Biochemicals) in the presence of an in vitro transcription reaction mixture, to obtain capped RNA. In the case of in vitro transcribed RNA, capping is preferably carried out during in vitro transcription, but can also be carried out during in vitro translation by, e.g., addition of a cap analog (GpppG or a methylated derivative thereof). Cap analogs and protocols pertaining to their use are commercially available, e.g, in in vitro transcription and/or translation kits.

The RNA for use in the invention preferably comprises most of the 5' end, at least enough of the 5' end of the RNA to contain a sufficiently long stretch of the signal sequence to encode a signal peptide that is sufficiently long to be capable of interacting with an SRP.

Exemplary Translation Systems

In order for RNA encoding proteins having a signal peptide to become attached to the ER or to microsomes, the RNA must be in the process of being translated. In fact, RNA sequence encoding the signal peptide must be essentially fully translated to allow attachment of the signal peptide to the SRP complex, which can then interact with an SRP receptor located on the outer surface of the rough ER or rough microsomes. Translation systems may be cellular or cell-free, and may be prokaryotic or eukaryotic cellular translation systems. Cellular translation systems, as used herein, refer to permeabilized cells. Cell-free translation systems, also referred to as "in vitro translation systems", refer to cell extracts and reconstituted systems.

In a preferred embodiment, the translation system is an in vitro translation system. A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes.

Mixtures of purified translation factors, as well as combinations of lysates or lysates supplemented with purified translation factors such as initiation factor-1 (IF-1), IF-2, IF-3 (alpha or beta), elongation factor T (EF-Tu) or termination factors can also be used for translation of RNA.

Translations in cell-free systems generally require incubation of the ingredients for a period of time sufficient to allow translation of mRNA into a polypeptide of sufficient length to enable the polypeptide to interact with a SRP complex. Incubation times may range from about 5 minutes to many hours, but is preferably between about thirty minutes to about five hours and more preferably between about one to about three hours. Incubation times vary significantly with the volume of the translation mix and the temperature of the incubation. Incubation temperatures can be between about 4° C. to about 60° C., and are preferably between about 15° C. to about 50° C., and more preferably between about 25° C. to about 45° C. and even more preferably at about 25° C. or about 37° C. Translation mixes will typically comprise buffers such as Tris-HCl, Hepes or another suitable buffering agent to maintain the pH of the solution between about 6 to 8, and preferably at about 7. Other reagents which may be included in the translation system include dithiothreitol (DTT) or 2-mercaptoethanol as reducing agents, RNasin to inhibit RNA breakdown, and nucleoside triphosphates or creatine phosphate and creatine kinase to provide chemical energy for the translation process. Preferred translation systems and translation conditions are further described herein.

Translation may also be performed in a continuous manner wherein reagents are flowed into the system and nascent proteins removed or left to accumulate using a continuous flow system (A. S. Spirin et al., Science 242:1162–64, 1988). This process may be desirable for large scale production of nascent proteins.

In an illustrative embodiment, the in vitro translation system is a reticulocyte lysate, which is available commercially or can be prepared, e.g., according to methods known in the art and briefly outlined below. Commercially available reticulocyte lysates are available from, for example, New England Nuclear and Promega Corp. (Madison, Wis.) (Cat. #L4960, L4970, and L4980). In another embodiment, the in vitro translation system is a wheat germ translation system. Such a system is also available commercially or can be prepared according to methods known in the art. Commercially available wheat germ extracts can be obtained, e.g., from Promega Corp. (Madison, Wis.) (e.g., Cat #L4370). In yet another preferred embodiment, the in vitro translation system is a mixture of a reticulocyte lysate and a wheat germ extract. Such a mixture can be obtained commercially, e.g., from Promega Corp. (Madison, Wis.) (e.g., Cat. #L4340). Other in vitro translation systems that can be used according to the method of the invention include *Escherichia coli* extracts, insect cell extracts and frog oocytes extracts.

To further illustrate, in vitro translation systems can be prepared by several methods. For example, a rabbit reticulocyte lysate can be prepared as follows. Rabbits are rendered anemic by inoculation with acetylphenylhydrazine. About 7 days later, the rabbits are bleeded and the blood is collected and mixed with an ice cold salt solution containing NaCl, Mg acetate, KCl, and heparin. The blood is then filtered through a cheesecloth, centrifuged, and the buffy coat of white cells is removed. The pellet consisting of erythrocytes and reticulocytes is then washed with the salt solution, prior to being lyzed by the addition of an equal volume of cold water. Endogenous RNAs are degraded by treating the lysate with micrococcal nuclease and calcium ions (necessary for the activity of the enzyme) and the reaction stopped by the addition of EGTA, which chelates the $CaCl_2$ and thereby inactivate the nuclease. Hemin is usually added to the lysate (at a concentration of about 20–80 $\mu$M), since it is a powerfull suppressor of an inhibitor of the initiation factor eIF-2. The lysates can further be optimized by the addition of an energy generating system, consisting of phosphocreatine kinase and phosphocreatine. The lysates can then be aliquoted and stored at –70° C. or in liquid nitrogen. Further details regarding this protocol are set forth, e.g., in Molecular Cloning A Laboratory Manual, 2nd Ed., ed. by Sambrook, Fritsch and Maniatis (Cold Spring Harbor Laboratory Press: 1989).

A wheat germ extract can be prepared, e.g., by the method described by Roberts, B. E. and Paterson, B. M. (1973), Proc. Natl. Acad. Sci. USA Vol. 70, No. 8, pp. 2330–2334), which optionally can be modified according to Anderson, C. W., et al. (1983, Meth. Enzymol. Vol. 101, p. 635). This protocol can further be modified according to the manufacturing protocol L418, Promega Corp. Madison, Wis. Generally, wheat germ extract is prepared by grinding wheat germ in an extraction buffer, followed by centrifugation to remove cell debris. The supernatant is then separated by chromatography from endogenous amino acids and plant pigments that are inhibitory to translation. The extract is also treated with micrococcal nuclease to destroy endogenous mRNA, to reduce background translation to a minimum. The extract contains the cellular components necessary for protein synthesis, such as tRNA, rRNA and initiation, elongation, and termination factors. The extract can further be optimized by the addition of an energy generating system consisting of phosphocreatine kinase and phosphocreatine, and magnesium acetate is added at a level recommended for the translation of most mRNA species. The final magnesium concentration for standard wheat germ extract, is typically in the range of about 6.0 to 7.5 mM.

A wheat germ cell in vitro translation system can also be prepared as follows. Wheat germ embryo extracts are floated to enrich for embryos using a mixture of cyclohexane and carbon tetrachloride (1:6), followed by drying overnight (about 14 hours). Floated wheat germ embryos (5 g) are then grounded in a mortar with 5 grams of powdered glass to obtain a fine powder. Extraction medium (Buffer I: 10 mM trisacetate buffer, pH 7.6, 1 nM magnesium acetate, 90 mM potassium acetate, and 1 mM DTT) is be added to small portions until a smooth paste is obtained. The homogenate containing disrupted embryos and 25 ml of extraction medium is centrifuged twice at 23,000×g. The extract is applied to a Sephadex G-25 fine column and eluted in Buffer II (10 mM trisacetate buffer, pH 7.6, 3 mM magnesium acetate, 50 mM potassium acetate, and 1 mM DTT). A bright yellow band migrating in void volume is collected (S-23) in one ml fractions and frozen in liquid nitrogen for conservation prior to use in in vitro translation reactions.

An in vitro translation reaction using a reticulocyte lysate can be carried out as follows. Ten $\mu$l of a reticulocyte lysate, e.g., prepared as set forth above or a commercial lysate, is mixed with spermidine, creatine phosphate, amino acids, HEPES buffer (pH 7.4), Kcl, magnesium acetate and RNA to be translated and incubated for an appropriate time, e.g., one hour, at 30° C. The optimum amount of magnesium acetate for obtaining efficient translation will vary from one reticulocyte lysate to another, and can be determined using a standard preparation of RNA and concentration of magnesium acetate varying from 0–1 mM. The optimal concentration of KCl can also be different depending on the specific reaction. For example, 70 mM KCl is usually optimal for translation of capped RNAs and 40 mM is usually optimal for translation of uncapped RNAs. To follow the translation process, one can add one or more amino acids as radioactive amino acids, e.g., $^{35}S$ methionine (further described below). In this case, the translation process can be monitored by precipitating the proteins in the lysate, e.g., TCA precipitating and counting the amount of radioactivity present in the precipitate. The translation products can also be analyzed by immunoprecipitation and/or SDS-polyacrylamide gel electrophoresis. Further details regarding this protocol are set forth, e.g., in Molecular Cloning A Laboratory Manual, 2nd Ed., ed. by Sambrook, Fritsch and Maniatis (Cold Spring Harbor Laboratory Press: 1989).

Translations in wheat germ extracts can be performed as described, e.g., in Erickson and Blobel (1983) Methods Enzymol. 96:38. This protocol can also be modified, e.g., by adjusting the final ion concentrations at 2.6 mM magnesium and 140 mM potassium and the pH at 7.5 (as described in U.S. Pat. No. 4,983,521). In a preferred embodiment, reaction mixtures are incubated at 24° C. for 60 minutes. Translations in wheat germ extracts can also be performed according to the protocol set forth in U.S. Pat. No. 5,492,817.

Translation reactions can be optimized by the addition of ions and/or other reagents. For example, magnesium is known to be important for optimizing translation, as it enhances the stability of assembled ribosomes and functions in their binding together during translation. Magnesium also appears to play a role in facilitating polymerase binding. Potassium is important as well for optimizing translation, but unlike the case for magnesium, for coupled transcription and translation the concentration of potassium ions does not need to be altered beyond standard translation preparation levels.

Potassium and magnesium are present in the standard rabbit lysate and are provided in part by the lysate itself, and in part by the addition of exogenous potassium and magnesium. As the magnesium concentration should be adjusted to within a rather narrow optimal range, it is preferred that the lysate magnesium levels be measured directly through the use of a magnesium assay, prior to the addition of extra magnesium, so that the amount of magnesium in a reaction can be standardized from one batch of lysate to the next. The Lancer "Magnesium Rapid Stat Diagnostic Kit" (Oxford Lab Ware Division, Sherwood Medical Co., St. Louis, Mo.), is one such assay which can accurately measure the magnesium levels in biological fluid. Once the magnesium ion concentration for a given batch of lysate is known then additional magnesium, for instance in the form of a concentrated magnesium salt solution, can be added in a known manner to bring the magnesium concentration of the lysate to within the optimal range, or, in the case of a modified lysate preparation to be used as one-half of a reaction mixture, to within twice the optimal range. Magnesium concentration can be adjusted by using, e.g., a concentrated solution of magnesium chloride or magnesium acetate.

One common addition to translation reactions is an amount of a polyamine sufficient to stimulate the efficiency of chain elongation. For example, spermidine can be added to a reticulocyte lysate translation reaction to a final concentration of about 0.2 mM. Spermidine is also preferably added to wheat germ extracts, preferably at a concentration of about 0.9 mM. Since the presence of polyamines are known to lower the effective magnesium concentration for translation reactions, the presence of spermidine in translation reactions should be taken into consideration when determining the appropriate concentration of magnesium to use.

In another embodiment, dithiothreitol (DTT) is added to the translation mixture. DTT is preferably added to a final concentration of about 1.45 mM in reticulocyte lysates and at 5.1 mM in wheat germ extracts.

Translation systems can also be supplemented with certain factors, e.g., tRNA molecules. Such molecules are commercially available, e.g., from a number of sources and can be prepared using well-known methods from sources including *Escherichia coli*, yeast, calf liver and wheat germ cells (Sigma Chemical; St. Louis, Mo.; Promega Corp.; Madison, Wis.; Boehringer Mannheim Biochemicals; Indianapolis, Ind.). Their isolation and purification mainly involves cell-lysis, phenol extraction followed by chromatography on DEAE-cellulose. Amino-acid specific tRNA, for example tRNA<fMet>, can be isolated by expression from cloned genes and overexpressed in host cells and separated from total tRNA by techniques such as preparative polyacrylamide gel electrophoresis followed by band excision and elution in high yield and purity (Seong and RajBhandary, Proc. Natl. Acad. Sci. USA 84:334–338, 1987).

Translation efficiency can also be improved, e.g., by adding RNAase inhibitors, e.g., RNasin® or heparin to the translation reaction. RNasin® can be obtained, e.g., from Promega Corp. (Madison, Wis.) (e.g., Cat #N2514). In a preferred embodiment about 40 units of RNasin® are added to a 50 μl reaction. Although the addition of RNAase inhibitors in reticulocyte lysates is not crucial, translation in a wheat germ extract is reduced if no RNAase inhibitor is added.

The translation reaction is preferably carried out from about 30 minutes to about 120 minutes prior to the addition of microsomes or in the presence of microsomes, such that a sufficient amount of the signal peptide has been translated to allow its binding to the SRP on the microsomes. The optimum time of translation can be determined, e.g., by labeling the RNA, e.g., by in vitro transcribing RNA in the presence of a labeled, e.g., radioactively labeled ribonucleotide, contacting the labeled RNA with an in vitro translation system, and measuring the amount of label associated with the microsomes over time. The optimal time is the time at which the maximum amount of label, thus RNA, is associated with the microsomes.

In a preferred embodiment, the translation process, including the movement of the ribosomes on the RNA molecules, is inhibited at an appropriate time by the addition of an inhibitor or translation, e.g., cycloheximide. Accordingly, in one embodiment, cycloheximide is added at a final concentration of 1 μg/ml to the translation reaction, which contains or does not contain microsomes. $Mg^{2+}$, e.g., $MgCl_2$, e.g., at a concentration of 5 mM can also be added to maintain the mRNA-80s ribosome-nascent polypeptide complexes (polysomes).

Translation of mRNA in an vitro system can be followed, e.g., by including a labeled amino acid in the translation reaction, and using an amino acid mixture depleted in this specific amino acid. A preferred labeled amino acid is a radioactively labeled amino acid, e.g., $^{35}S$ methionine. Alternatively, a labeled non-radioactive amino acid can be incorporated into the nascent polypeptide. For example, the translation reaction can comprise a misaminoacylated tRNA, as described in U.S. Pat. No. 5,643,722. Accordingly, a non-radioactive marker, is misaminoacylated to a tRNA molecule and this tRNA is added to the translation system. The system is incubated to incorporate the marker into the nascent polypeptide and polypeptides containing the marker can be detected using a detection method appropriate for the specific marker.

Useful markers are native amino acids coupled with a detectable label, detectable non-native amino acids, detectable amino acid analogs and detectable amino acid derivatives. Labels and other detectable moieties may be ferromagnetic, paramagnetic, diamagnetic, luminescent, electrochemiluminescent, fluorescent, phosphorescent or chromatic. Fluorescent moieties which are useful as markers include dansyl fluorophores, coumarins and coumarin derivatives, fluorescent acridinium moieties and benzopyrene based fluorophores. Preferably, the fluorescent marker has a high quantum yield of fluorescence at a wavelength different from native amino acids. Upon excitation at a preselected wavelength, the marker is detectable at low concentrations either visually or using conventional fluorescence detection methods. Electrochemiluminescent markers such as ruthenium chelates and its derivatives or nitroxide amino acids and their derivatives are preferred when extreme sensitivity is desired (J. DiCesare et al., BioTechniques 15:152–59, 1993). These markers are detectable at the fentomolar ranges and below. Biotin, streptavidin and derivatives thereof can also be used to label amino acids. These and other markers for labeling amino acids for detection of nascent polypeptides are disclosed in U.S. Pat. No. 5,643,722.

In another embodiment of the invention, the in vitro transcription and translation reactions are performed simultaneously. This can be done, e.g., by using commercially available systems, such as the Coupled Transcription/Translation System of Promega Corp. (Madison, Wis.) (Cat #L4600, 4610, and 4950). Coupled transcription and translation systems using RNA polymerases and eukaryotic lysates are further described in U.S. Pat. No. 5,324,637.

Cell-based translation systems, e.g., permeabilized cells, can be prepared as follows. Cells can be permeabilized by incubation for a short period of time in a solution containing low concentrations of detergents in a hypotonic media. Useful detergents include Nonidet-P 40 (NP40), Triton X-100 (TX-100) or deoxycholate at concentrations of about 0.01 nM to 1.0 mM, preferably between about 0.1 mu M to about 0.01 mM, and more preferably about 1 $\mu$M. Such systems can be formed from intact cells in culture such as bacterial cells, primary cells, immortalized cell lines, human cells or mixed cell populations.

Exemplary ER preparations

In preferred embodiments, the ER preparations used to generate the subject reaction systems are microsomal preparations. Microsomes can be added to the in vitro translation system at the same time as the RNA, such that the RNA becomes attached to the microsomes as soon as the length of the growing peptidic chain is sufficient for allowing attachment of the signal peptide to the SRP. Alternatively, translation can be carried out for a specific amount of time and the microsomes can then be added to the translation reaction. Optionally, inhibitors of translation can be added at an appropriate time to the reaction. In one embodiment, the RNA is contacted with an in vitro translation system for about 30–120 minutes prior to the addition of microsomes. As set forth above, the optimum amount of time for incubation of the RNA with an in vitro translation system can be determined, e.g., by performing small scale assays in which the RNA is labeled, translated for various amounts of time, contacted with microsomes, and the amount of labeled RNA attached to the microsomes is determined.

Microsomes are commercially available. For example, canine pancreatic microsomal membranes are available from Promega Corp. (Madison, Wis.) (Cat. #Y4041). Microsomes for use in the invention, can also be prepared according to methods known in the art, e.g., as described in Walter and Blobel (1983) Methods Enzymol. 96:682), or a modification thereof, as described in U.S. Pat. No. 4,983, 521. Briefly, a cell or tissue can be homogenized, subjected to low speed centrifugation to pellet nuclei, mitochondria, and cell debris, leaving the microsomes (rough and smooth) in suspension. The supernatant can then be subjected to a sucrose density gradient, which after centrifugation to equilibrium results in the separation of the rough and smooth microsomes due to their different densities. Rough microsomes are denser and can be recovered as a lower band in the sucrose gradient compared to the smooth microsomes. Endogenous RNA attached to the microsomes can be detached from the microsomes, by, e.g., incubating the microsomes with an RNAse. Alternatively, the RNA can be removed from the microsomes by incubation of the microsomes in a high salt solution. In another embodiment, the microsomes are prepared by reconstitution.

Microsomes can be added to a translation system or a solution containing RNA that is at least partially translated at a concentration of from about 1.2 to about 5 A280 U/ml. Microsomes are preferably added at a concentration of about 3, 4, or 5 A280 U/ml.

In a specific embodiment, the invention provides for isolation and cloning of an RNA molecule isolated from microsomes that are isolated from a specific cell or tissue sample. For example, microsomes are prepared from a specific cell or tissue sample, e.g., by homogenization of the cell or tissue, low speed centrifugation and centrifugation of the supernatant containing the microsomes in a sucrose density gradient, as further described herein. The rough microsomes are then isolated from the gradient and one or more RNA molecules are isolated therefrom.

Exemplary Purification of Microsome/RNA Complexes and Isolation of RNA from the Microsome/RNA Complexes Following incubation of RNA, an in vitro translation system, and microsomes for an appropriate amount of time to generate at least partially translated RNA molecules associated with microsomes, the microsomes are isolated from the reaction mixture.

In one embodiment, the microsomes are isolated from the mixture containing the microsomes, the RNA, and the translation reaction by subjecting the reaction mixture to a sucrose density gradient centrifugation, such that the microsomes and the RNA associated therewith ("microsomes/RNA complexes) form a band, whereas the free ribosomes and other elements of the reaction mixture are pelleted. The band containing the microsomes/RNA complexes, which also contain the polypeptide attached thereto, is isolated from the centrifugation tube. Thus, this fraction will contain the RNA associated with microsomes, i.e., RNA containing a signal sequence.

The RNA associated with the microsomes can be isolated by various methods. In a preferred embodiment, the isolated (bound) polysomes are disrupted by removal of $Mg^{2+}$, e.g., by dilution, via chelating agents or through the destruction of proteins by any number of methods, e.g., proteases, chlorophorm and/or phenol or any other agent for isolating RNA.

Alternatively, the ribosomes can be first separated from the endoplasmic membrane, e.g., by the addition of a detergent. Ribosomes can also be released from the membranes by methods which do not use detergents, as described, e.g., in Harrison et al. (1974) Eur. J. Biochem. 47:613. The RNA can then be separated from the ribosomes, e.g., by using at least one protease or by performing a phenol extraction.

The preparation of RNA encoding proteins having a signal peptide can be enriched in RNA encoding proteins having specific characteristics. Accordingly, the polyribosomes, which contain RNA and the growing peptidic chain, are separated from the microsomal membranes and screened for polypeptides having a specific activity prior to isolation of the RNA. In this embodiment, it is preferred that translation be continued for a longer time, such that longer peptidic chains are synthesized. It is also preferable in this embodiment to use an agent that cause the polyribosome/RNA/polypeptide to separate from the ER membrane without significantly affecting the polypeptide or the RNA molecules of the complex. The ER membrane can also be dissolved. For example, mild detergents, e.g., non ionic detergents can be used. In an illustrative embodiment, the polyribosomes isolated from microsomes, can be screened for their capacity to interact with a specific molecule, e.g., a receptor. This can be achieved, e.g., by contacting the polyribosomes with a soluble or membrane bound receptor and isolating the polyribosomes which interact with the receptor. The RNA from these polyribosomes, which encode the polypeptide having the specific activity screened for, can then be extracted.

The nascent polypeptidic chain attached to the polyribosome can also be screened for interaction with surface antigens, toxins, organic polymers, antibodies, metabolites, hormones, and active sites of protein molecules. As set forth above, a compound can be linked to a solid surface. A solid surface can be, e.g., a membrane, beads, e.g., magnetic beads, a column or the surface of a plate. The coupling chemistries to link a compound to a specific surface will depend on the compound and the specific surface. For example, many proteins and nucleic acids can be attached to membranes and e.g., cross-linked to the membrane. In preferred embodiments, bovine serum albumin (BSA), gelatin, casein, nonfat milk or other proteinous material is typically added in excess to bind up any "free" surface sites prior to contacting with the polyribosomes. This preabsorption step is likely to lead to much greater binding specificity of the polysomes to the compound of interest. The binding of polysomes to substances of interest may be performed in the presence of $MgCl_2$ (preferably 5 mM) and/or RNAse inhibitors. In addition, specific incubation parameters, such as low or high temperature, high or low salt, or different pHs, may be used to identify peptides which bind conditionally, i.e., depending on their environment. Incubation times may depend on the concentration of the bound compound of interest and on the nature of the compound of interest.

After allowing the polysomes to bind to the substance of interest, non-binding polysomes can be removed, e.g., by washings. The wash preferably contains $MgCl_2$ and optionally gelatin, BSA, or other proteinous material to reduce non-specific binding. The RNA from the selected polysomes can then be extracted as described above and used, e.g., for preparing a library of nucleic acids.

In some embodiment, binding of polyribosomes to whole cells or cell extracts is also considered. The polyribosomes can also be screened for a specific biological activity, e.g., an enzymatic activity. In this embodiment, the polyribosomes isolated from the microsomes can be grouped into pools, which are screened for a specific function, e.g., nuclease or protease activity. Once a positive pool has been identified, the RNA can be extracted, optionally amplied, e.g, by RT-PCR, resubjected to in vitro transcription/translation in the presence of microsomes, and rescreened for the particular biological activity of interest. Biological activities of interest also include stimulation or inhibition of cell proliferation, differentiation, and induction of cell death.

Cloning of RNA Molecules Isolated from Microsomes and/or Preparation of a Library In one embodiment of the invention, at least one single stranded DNA molecule is synthesized from at least one RNA molecule isolated from the microsomes.

A first strand DNA can be synthesized from RNA by various methods known in the art. In a preferred embodiment of the invention, a first cDNA strand is synthesized by reverse transcription using a reverse transcriptase and a primer, e.g., an oligodT primer.

In a preferred embodiment of the invention, the single stranded DNA molecule is converted into a double stranded cDNA molecule. A second cDNA strand can be synthesized according to various methods known in the art. In a preferred embodiment, the second cDNA strand is synthesized by Okayama and Berg method modified by Gubler and Hoffman, in which the product of the first strand synthesis, a cDNA-mRNA hybrid, is used as a template for a nick-translation reaction using RNAase H and a polymerase. According to the method, RNAase H produces nicks and gaps in the mRNA strand of the hybrid, creating a series of RNA primers that are used by *E. coli* DNA polymerase I during the synthesis of the second strand of cDNA.

In another embodiment, the second strand is synthesized by self-priming. Accordingly, the cDNA-mRNA hybrid is denatured by boiling or the RNA is hydrolyzed by NaOH and the second strand is primed by the 3' end of the first cDNA strand which forms a hairpin loop. The second strand is then extended from the self-primer by using, e.g., Klenow fragment of *E. coli* DNA Polymerase I. The hairpin loop can then be eliminated by, e.g., digestion with nuclease S1, which degrades single stranded DNA.

In yet another method of the invention, the second strand is synthesized as follows. After completion of the first strand synthesis, terminal transferase is used to add homopolymeric tails of C residues to the free 3' OH end. This tail is then hybridized to oligodG, which serves as a primer for synthesis of a full-length second strand of cDNA.

All of the above methods and others for synthesizing a first and second cDNA strand are described in detail, e.g., in Molecular Cloning A Laboratory Manual, 2nd Ed., ed. by Sambrook, Fritsch and Maniatis (Cold Spring Harbor Laboratory Press: 1989).

In a preferred method of the invention, the single or double stranded cDNA is inserted into a vector or a plasmid. In an even more preferred embodiment, a population of cDNAs is cloned in a vector to form a library, e.g., a cDNA library.

The first and second strand of cDNA molecules and preparation of a cDNA library can also be constructed using commercially available kits, e.g., the Superscript Plasmid System for cDNA synthesis and Plasmid Cloning Kit (Life Technologies, Gaithersburg, Md.).

Yet other methods for cloning the isolated RNA molecule (s) include techniques based on polymerase chain reaction (PCR). For example, the RNA molecules can be reverse transcribed into a first strand DNA, a second strand is synthesized and the DNA is then used in a PCR reaction. Oligonucleotides can be linked to both ends of the DNA prior to amplification with primers hybridizing to these oligonucleotides. One can also use the amplifed DNA for further enrichment in DNA sequences encoding proteins containing a signal peptide. For example, the DNA population can be cloned into a vector, the DNA is transcribed into RNA, in vitro translated and contacted with microsomes and the RNA associated with the microsomes is isolated.

In one embodiment, the nucleotide sequence of individual clones of the library is determined, to identify secreted proteins. The nucleotide sequence of the isolated nucleic acid and the protein encoded thereby can be compared to the nucleotide and amino acid sequences present in GenBank to determine if the nucleic acid and/or protein is homologous to known nucleic acids and proteins. In vitro assays can then be used to determine whether the protein cloned is a secreted protein or a protein associated with a cellular membrane. For example, a nucleic acid encoding a "TAG", e.g., myc tag or a tag consisting of a 16 amino acid portion of the *Haemophilus influenza* hemagglutinin protein (Cross et al. (1984) Mol. Cell. Biol. 4:1834), can be linked to the nucleic acid of interest, the nucleic acid and the tag can be inserted into an expression vector, transfected into host cells and the location of the "TAG" is then determined using a reagent that specifically detects the "TAG". Other useful epitope tags include myc-epitopes (e.g., see Ellison et al. (1991) *J Biol Chem* 266:21150–21157) which includes a 10-residue sequence from c-myc, as well as the pFLAG system (International Biotechnologies, Inc.) or the pEZZ-protein A system (Pharamacia, N.J.) The reagent can be an antibody, e.g., Ab 12CA5, which specifically interacts with the *H. influenza* TAG peptide and can be obtained, e.g., from Babco, Richmond Calif. The location of the tagged protein can be determined, e.g., by monitoring the presence of the TAG in the supernatant, such as by immunoprecipitations using the supernatant of the transfected cells. The presence of the protein in the supernatant of the cell culture will be indicative that the protein is in fact a secreted protein. If the protein is not a secreted protein, the cellular location of the protein can be determined by performing immunohistochemistry experiments using a reagent binding specifically to the TAG, e.g., an antibody. These assays will indicate whether the cloned nucleic acid encodes a secreted protein or a membrane associated protein, as well as to which membrane the protein is associated.

Various assays known in the art can be used to determine the activity of the newly cloned gene. Some available assays are described, e.g., in U.S. Pat. No. 5,728,819 by Jacobs et al. issued on Mar. 17, 1998.

In another embodiment, the cDNA library is screened with a specific probe. For example, if one wishes to isolate a nucleic acid encoding a secreted protein that is homologous to a known secreted protein, the cDNA library can be screened under low stringency conditions with a nucleic acid encoding the protein.

In another preferred embodiment of the invention, the cDNA library is an expression library. The expression library can be a prokaryotic expression library, e.g., a bacterial expression library. Alternatively, the expression library can be a eukaryotic expression library, which can be introduced and expressed, i.e., in yeast cells, or in vertebrate cells, such as mammalian cells, preferably human cells. An expression library can be screened by various methods, e.g., binding of the secreted protein to a ligand, receptor, or antibody, or a biological function, as set forth below.

In a preferred embodiment, the expression library is divided into pools of clones, which are screened to identify a particular pool, which is then divided into subpools, which are screened, redivided several times until one or more clones having the desired activity are isolated. The screening method can be based on a specific biological function, e.g., screening with a receptor for the identification of a ligand of a receptor, e.g., an orphan receptor. The screening method can also be based on a specific biological activity, e.g., an enzymatic activity, e.g., stimulation or inhibition of cellular growth, stimulation or inhibition of differentiation of one or more cell types, induction or prevention of apoptosis, degradation of the extracellular matrix, and others.

Expression vectors of utility in the present invention are often in the form of "plasmids", which refer to circular double stranded DNA loops which, in their vector form, are not bound to the chromosome. However, the invention is intended to include such other forms of expression vectors which serve equivalent functions and which become known in the art subsequently hereto.

Expression vectors useful in the present invention typically contain an origin of replication, a promoter located in front of (i.e., upstream of) the DNA sequence and followed by the DNA sequence of interest, transcription termination sequences and the remaining vector. The expression vectors may also include other DNA sequences known in the art, for example, stability leader sequences which provide for stability of the expression product, secretory leader sequences which provide for secretion of the expression product, sequences which allow expression of the structural gene to be modulated (e.g., by the presence or absence of nutrients or other inducers in the growth medium), marking sequences which are capable of providing phenotypic selection in transformed host cells, stability elements such as centromeres which provide mitotic stability to the plasmid, and sequences which provide sites for cleavage by restriction endonucleases. The characteristics of the actual expression vector used must be compatible with the host cell which is to be employed. For example, when cloning in a mammalian cell system, the expression vector should contain promoters isolated from the genome of mammalian cells, (e.g., mouse metallothionien promoter), or from viruses that grow in these cells (e.g., vaccinia virus 7.5K promoter). An expression vector as contemplated by the present invention is at least capable of directing the replication, and preferably the expression, of the DNA sequences of the present invention. Suitable origins of replication include, for example, a yeast ARS element, a COLEI ori element, and an SV40 ori element. Suitable promoters include, for example, the yeast GAL1 promoter, the synthetic bacterial Tac promoter, the SV40 early promoter and the baculovirus AcNPV polyhedrin promoter. Suitable termination sequences include, for example, the yeast cycl terminator, the bacterial rrnB terminator, and the SV40 3' polyA' signal segment. As selectable markers, kanamycin resistance, uracil (URA3) marker and neomycin resistance can be employed. All of these materials are known in the art and are commercially available.

Preferred expression vectors contain a "TAG" sequence located either upstream or downstream of the restriction sites for inserting the DNA of interest, such that the DNA of interest is expressed as a TAG fusion protein. The presence of a TAG on a protein facilitates detection and purification of the protein. In one embodiment, the TAG is a myc tag. In another embodiment, the TAG is a hexahistidine tag, which binds with high affinity to nickel.

Suitable expression vectors containing the desired coding and control sequences may be constructed using standard recombinant DNA techniques known in the art, many of which are described in Molecular Cloning A Laboratory Manual, 2nd Ed., ed. by Sambrook, Fritsch and Maniatis (Cold Spring Harbor Laboratory Press: 1989).

In another embodiment, the RNA isolated from the microsomes is amplified and subjected to a second round of screening for signal sequences. For example, the RNA molecules can be amplified using RNA-directed RNA polymerases. Alternatively, cDNA can be prepared from the RNA, the cDNA cloned into a vector downstream of a promoter, e.g., SP6, T3, or T7 promoter, such that the cloned cDNA can be in vitro transcribed. The in vitro transcribed RNA, which has preferably been capped during the in vitro transcription reaction, can then be in vitro translated and contacted with microsomes as described in the first round of selection. Yet further rounds of enrichment can be performed.

Accordingly, the method of the invention permits isolation of nucleic acids encoding proteins having a signal sequence, e.g., secreted proteins. Secreted proteins can be cell growth and/or differentiation factors, e.g., cytokines, interleukins, colony stimulating factors and others.

The invention further provides cells, also termed herein "host cells" comprising a vector including a cloned nucleic acid of the invention. Such cells can be used, e.g., for the production of high amounts of secreted proteins, which can be used, e.g., for preparing pharmaceutical compositions. Host cells can be prokaryotic, e.g., bacterial, or eukaryotic, e.g., yeast cells, e.g., *S. cerevisiae*, and *S. pombe*, vertebrate cells, preferably mammalian cells, even more preferably human cells. Expression in a eukaryotic host cells has the advantage that proteins can be posttranslationally modified, e.g., glycosylated. Preferred eukaryotic cells for expression of a protein of the invention include COS monkey cells and CHO cells.

The invention further provides proteins encoded by the nucleic acids of the invention. Such proteins can be produced, e.g., from host cells transfected with the nucleic acids of the invention. Proteins can be produced according to methods known in the art, such as by culturing host cells comprising a nucleic acid of the invention in conditions suitable for the production of the protein encoded by the nucleic acid, and isolation of the protein from the culture medium and/or the host cells.

Also within the scope of the inventions are non-human transgenic animals containing a nucleic acid identified according to the method of the invention. The term transgenic animals includes animals in which a nucleic acid of the invention is introduced into the animal and is integrated into the genome of the animal or an animal in which the endogenous gene corresponding to a gene of the invention has been mutated, e.g., by the insertion of an unrelated nucleic acid (e.g., "knock-out" mutant).

The invention also provides kits containing reagents for performing the invention. Such reagents can include one or more of an in vitro transcription system, an in vitro translation system, microsomes, and reagents and buffers for isolating the microsome/polyribosome complexes and/or the RNA, reagents for synthesizing a first stand DNA, reagents for synthesizing a second strand of DNA, reagents for preparing a library, and oligonucleotides and primers for amplification of the DNA. Other kits within the scope of the invention contain one or more of the newly cloned DNA molecules.

Exemplary Uses of the Invention

The nucleic acids of the invention, e.g., encoding secreted proteins, can have various utilities, in particular therapeutic utilities. Sequence analysis of the nucleic acid and amino acid sequences will reveal whether the nucleic acid and/or amino acid sequence have any particular motifs characteristic of certain types of proteins. Furthermore, comparison of the nucleic acid and amino acid sequences with known sequences will reveal whether the newly cloned nucleic acid or protein has any homology to known nucleic acids or proteins. In addition, in vitro and in vivo experiments can be performed to determine whether the nucleic acid encodes a protein having a particular biological activity, e.g., cell growth and/or differentiation stimulatory activity. Thus, based on at least this information, the nucleic acid and/or protein encoded thereby can be used for treating or preventing specific diseases or disorders. For example, if the protein has a cell growth stimulatory activity, the protein could be used for treating cell proliferative disorders, e.g., cancer.

The polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)) to identify polynucleotides encoding the other protein with which binding occurs or to identify inhibitors of the binding interaction.

The proteins provided by the present invention can similarly be used in assay to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Any or all of these research utilities are capable of being developed into reagent grade or kit format for commercialization as research products. In one embodiment, the invention provide a solid surface, e.g., a chip, to which are linked one or more polynucleotide or polypeptide cloned according to the method of the invention. Such solid surfaces can be commercialized and used by others for characterizing other proteins. In particular, these should be useful for identifying ligands of orphan receptors.

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

In one embodiment of the invention, a disease or disorder is prevented or treated in a subject, by administering to the subject an effective amount of a pharmaceutical composition comprising a secreted protein or a nucleic acid encoding a secreted protein and a pharmaceutically acceptable carrier. The nucleic acid can be a nucleic acid encoding the full length protein or a biologically active portion thereof. In one embodiment, the nucleic acid is operably linked to a promoter, such that upon entrance into a cell, the nucleic acid is transcribed and translated into a biologically effective protein. The promoter can be a constitutive promoter or an inducible promoter. In another embodiment, the protein is synthesized ex vivo and administered in an effective amount to the subject having a disease or disorder. The protein can be synthesized in any cell, e.g., prokaryotic cell, such as a bacterial cell, or a eukaryotic cell, e.g., a human cell according to methods known in the art.

Nucleic acids or proteins of the invention can be administered to a subject at therapeutically effective dose to treat or ameliorate a specific disease. A therapeutically effective dose refers to that amount of the compound sufficient to result in amelioration of symptoms associated with the particular disease.

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the nucleic acids and proteins of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the nucleic acids and proteins of the invention can be formulated in liquid solutions, preferably in physiologically compatible buffers such as Hank's solution or Ringer's solution. In addition, the nucleic acids and proteins of the invention may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound. For buccal administration the compositions may take the form of tablets or lozenges formulated in conventional manner.

For administration by inhalation, the nucleic acids and proteins of the invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insulator may be formulated containing a powder mix of the compound and a suitable powder base such as lactose or starch.

The nucleic acids and proteins of the invention may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The nucleic acids and proteins of the invention may also be formulated in rectal compositions such as suppositories or retention enemas, e.g., containing conventional suppository bases such as cocoa butter or other glycerides.

In addition to the formulations described previously, the nucleic acids and proteins of the invention may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the nucleic acids and proteins of the invention are formulated into ointments, salves, gels, or creams as generally known in the art.

In clinical settings, the gene delivery systems for the therapeutic gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054–3057). A therapeutic gene, can also be delivered in a gene therapy construct by electroporation using techniques described, for example, by Dev et al. ((1994) Cancer Treat Rev 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

In another embodiment, the secreted proteins isolated according to the method of the invention can be distributed in 96 well plates and made commercially available for high throughput screening of the proteins for a specific activity. Accordingly, in a specific embodiment, the secreted proteins are produced in vitro, e.g., in bacteria, and are then linked to the surface of the 96 well plate and made commercially available. Thus, high numbers of secreted proteins can be screened, e.g., for specific binding to a receptor.

The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. : 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

EXAMPLES

Example 1
Separation of RNA Encoding Secreted Proteins from RNA Encoding Non-secreted Proteins This example demonstrates that RNA encoding a secreted protein can be separated from RNA encoding a non-secreted protein. The technique used, which is outlined in FIG. 1, is based on the fact that secreted proteins are bound to microsomes as they are being translated, bringing along their associated RNAs. The membrane vesicles (and associated RNAs) can then isolated on a discontinuous sucrose density gradient which causes the vesicles to float towards the top of the gradient, whereas the ribosomes, free polysomes, and other RNAs remain at the bottom of the gradient due to their higher densities. RNA molecules associated with microsomes can then be isolated.

Capped RNA encoding the secreted protein FGF Related Ligand 2 (FRL2; Noriyuki et al. Cell 83:621) and RNA encoding the cytosolic protein ornithine decarboxylase (ODC; Bassez et al. Development 110:955) were each prepared separately as follows. Plasmid (pCS2+; Turner and Weintraub (1994) Genes Dev. 8:1434) containing DNA encoding each of the proteins were linearized downstream of the insert with the restriction enzyme NotI and used as template for the in vitro synthesis of RNA as described in Krieg and Melton (1984) Nucl. Acid. Res. 12, 7057–7070.

To show that the RNAs encoding the two proteins can be separated from each other, a mixture of the two RNAs was subjected to the procedure outlined in FIG. 1. Accordingly, 0.25 µg of each of the synthesized RNAs were then mixed together and the mixture was incubated for 1 hour at 30° C. in a 30 µl reaction containing 20 µl nuclease treated rabbit reticulocyte lysate (Promega), 45 units of Rnasin (Promega), 15 µM complete amino acid mix (Promega), and 0.2 mg/ml rabbit liver tRNA (Sigma) with or without 2 µl canine pancreatic microsomal membranes (Promega). After the incubation, the reactions were mixed with 90 µl of dilution buffer (50 mM Hepes, pH 7.5; 500 mM Kcl; 5 mM $MgCl_2$; 1 mM DTT; 1 mg/ml rabbit liver tRNA) containing 2.9 M sucrose (final sucrose concentration of the mixtures was about 2.2M). The mixtures were then applied to the bottom of Beckman Ultra-Clear™ 5×41 mm centrifuge tubes and layered with 150 µl, 200 µl, 50 µl, and 25 µl of dilution buffer containing, 2.0 M, 1.8 M, 0.3 M, and 0.0 M Sucrose respectively. Samples were then centrifuged in a Beckman Sw50 ultracentrifuge rotor at 50,000 rpm for 5 hours at 4° C. After centrifugation, three fractions (180 µl each) were collected successfully by pipetting from the top of the centrifuge tube and processed for reverse transcription-polymerase chain reaction (RT-PCR).

Each of the fractions were extracted with 1 mL of Rnazol B (Tel-Test) followed by extraction with an equal volume of chloroform. Total RNAs were precipitated with 2-propanol, wahsed with 70% ethanol, and resuspended with 14 µl of water containing 0.05 units of a reverse primer encoding a common vector sequence (5'ACC TCC CCC TGA ACC TGA AAC 3'; SEQ ID NO: 1) present within the 3' untranslated region of all in vitro transcripts generated from the pCS2+ vector. Reverse transcription was performed with the addition of RT buffer (1X final; Promega), 1 mg/ml BSA, 1 mM DTT, 25 mM dNTP, 20 units RNAsin, and 100 units MMLV-RT (Promega). Samples were incubated at 42° C. for 30 minutes. PCR was carried out in 10 µl reactions consisting of 0.5 units Taq DNA polymerase (Promega), 2.5 mM $MgCl_2$, 100 µM dNTP, 0.5 µCi[ $^{32}$-P]dCTP, 1 µl of the reverse transcribed reaction, and 10 pmol of each primer. The following primers were used in the PCR reactions: FRL2 forward primer 5'ATG CTT GAC ATT ATG GTG 3'( SEQ ID NO: 2); FRL2 reverse primer 5'TTA TCT CAT AGC AGG GAG 3'(SEQ ID NO: 3); ODC forward primer 5'AAT GGA TTT CAG AGA CCA 3'( SEQ ID NO: 4); and ODS reverse primer 5'CCA AGG CTA AAG TTG CAG 3'(SEQ ID NO: 5). 29 cycles were performed at the following temperatures: 94° C. for 1 minute, 55° C. for 1 minute, and 72° C. 1 minute. A sample of each of the PCR reactions was then separated on an agarose gel and ethidium bromide stained to visualize the amplified products.

Figure 2:
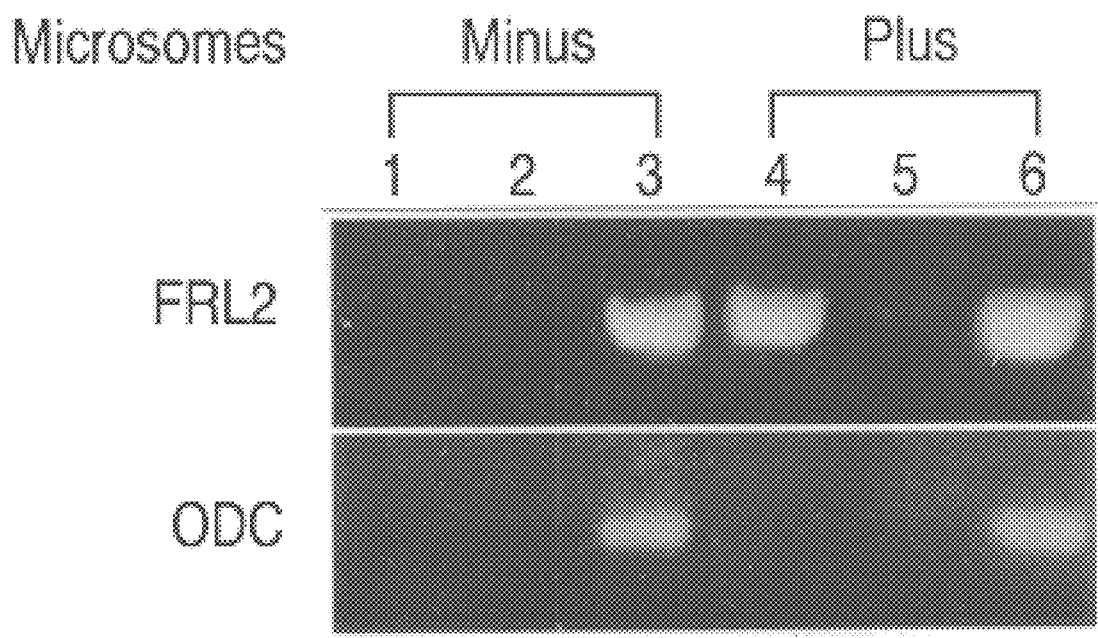
FIG. 2 is a photograph of an agarose gel showing RT-PCR amplified FRL2 and ODC RNA isolated from the top, middle and bottom of a sucrose gradient loaded with a translation reaction with ("Plus") or without ("Minus") microsomes.

A photograph of the agarose gel is shown in FIG. 2. The results indicate that in the absence of microsomes, messages encoding both FRL2 and ODC are present only at the bottom of the gradient. In the presence of microsomes, however, FRL2 (encoding a secreted protein) is found both at the top and bottom of the gradient, whereas ODC (encoding a cytosolic protein) is found exclusively at the bottom of the gradient.

Thus, this Example demonstrates that the procedure outlined in FIG. 1 allows the isolation of RNA encoding secreted proteins from RNA encoding non-secreted proteins.

Example 2
Isolation of RNA Encoding Secreted Proteins from Libraries

This example demonstrates that the technique used in the previous example and outlined in FIG. 1 can be used to isolate RNAs encoding secreted proteins or other proteins having a signal peptide from a mixture of RNAs transcribed from a cDNA library.

Capped RNA was prepared from a from a Xenopus stage 11-15 library as follows. The library was built into the vector pCS2+ (Turner and Weintraub (1994) Genes Dev. 8, 1434–1447) and was linearized with the restriction enzyme Not I to synthesize capped RNA in vitro as described previously (Krieg and Melton (1984), supra). For floating, 0.5 µg sample of the synthesized RNA was incubated for 1 hour at 30° C. in 30 µl reactions containing 20 µl nuclease treated rabbit reticulocyte lysate (Promega), 45 units of Rnasin (Promega), 15 µM complete amino acid mix (Promega), 2 µl canine pancreatic microsomal membranes (Promega), and 0.2 mg/ml rabbit liver tRNA (Sigma). The final reaction was then mixed with 90 µl of dilution buffer (50 mM Hepes, pH 7.5; 500 mM Kcl; 5 mM MgCl$_2$; 1 mM DTT; 1 mg/ml rabbit liver tRNA) containing 2.9 M sucrose (final sucrose concentration was about 2.2M). The mixture was then applied to the bottom of Beckman Ultra-Clear™ 5×41 mm centrifuge tubes and layered with 150 µl, 200 µl, 50 µl, and 25 µl of dilution buffer containing, 2.0 M, 1.8 M, 0.3 M, and 0.0 M Sucrose respectively. Samples were then centrifuged in a Beckman Sw50 ultracentrifuge rotor at 50,000 rpm for 5 hours at 4° C.

After centrifugation, 5 fractions (110 µl each) were collected successively by pipetting from the top of the centrifuge tubes and processed for RT-PCR.

After centrifugation, each of the fractions were extracted with 1 mL of Rnazol B (Tel-Test) followed by extraction with an equal volume of chloroform. Total RNAs were precipitated with 2-propanol, wahsed with 70% ethanol, and resuspended with 14 µl of water containing 0.05 units of a reverse primer encoding a common vector sequence present within the 3' untranslated region of all transcripts (5'ACC TCC CCC TGA ACC TGA AAC 3'; SEQ ID NO: 1). Reverse transcription was performed with the addition of RT buffer (1X final; Promega), 1 mg/ml BSA, 1 mM DTT, 25 mM dNTP, 20 units RNAsin, and 100 units MMLV-RT (Promega). Samples were incubated at 42° C. for 30 minutes. PCR was carried out in 10 µl reactions consisting of 0.5 units Taq DNA polymerase (Promega), 2.5 mM MgCl$_2$, 100 µM dNTP, 0.5 µCi [ $^{32}$-P]dCTP, 1 µl of the reverse transcribed reaction, and 10 pmol of each primer. The sequences encoding the following secreted or cytosolic proteins were amplified: the secreted proteins Sonic Hedgehog, Epidermal Fibroblast Growth Factor (EFGF), Sizzled, Dickkopf, Follistatin, and Cerberus; and the cytosolic proteins: epidermal keratin (epid. Keratin), EFlalpha, Xtwist, Goosecoid, and Neurogenin. The following primers were used in the PCR reactions for detecing RNA encoding each of these proteins: sonic hedgehog forward 5'-TCCTCCAGACCAGACCTTCCA-3'(SEQ ID NO: 6), reverse 5'-CGTATTAGTTCGTTTGTTTGT-3'(SEQ ID NO: 7); eFGF forward 5'-GTGCCTGCCGCTTTCTTTCCA-3' (SEQ ID NO: 8), reverse 5'-AACTCACGACTCCAACTTCCA-3'(SEQ ID NO: 9); sizzled forward 5'-AGCCCTGCCGTAGTATGTGTG-3' (SEQ ID NO: 10), reverse 5'CTGTGGGTCTGGTCCGTATCA-3'(SEQ ID NO: 11); dickkopf forward 5'-AGATGATGACTGTGCCCTTGA-3' (SEQ ID NO: 12), reverse 5'-CCTTTCCTCCTGTGCTTGGTG-3'(SEQ ID NO: 13); follistatin forward 5'-CAGTGCAGCGCTGGAAAG-3' (SEQ ID NO: 14), reverse 5'-TGCGTTGCGGTAATTCAC-3'(SEQ ID NO: 15); cerberus forward 5'-TTCTCGCCGTTCTTTTGATAA-3'(SEQ ID NO: 16), reverse 5'-ACACGTGCATTCCTCTACCAT-3'(SEQ ID NO: 17). epidermal keratin forward 5'-CACCAGAACACAGATAC-3'(SEQ ID NO: 18), reverse 5'-CAACCTTCCCATCAACCA-3'(SEQ ID NO: 19); EFlalpha forward 5'-CAGATTGGTGCTGGATATGC-3'(SEQ ID NO: 20), reverse 5'-ACTGCCTTGATGACTCCTAG-3' (SEQ ID NO: 21); Xtwist forward 5'-AGTCCGATCTCAGTGAAGGGCA-3'(SEQ ID NO: 22), reverse 5'-TGTGTGTGGCCTGAGCTGTAG -3'(SEQ ID NO: 23); goosecoid forward 5'-ACAACTGGAAGCACTGGA-3'(SEQ ID NO: 24), reverse 5'- TCTTATTCCAGAGGAACC-3'(SEQ ID NO: 25); and neurogenin forward 5'-CAAGAGCGGAGAAACTGTGT-3'(SEQ ID NO: 26), reverse 5'-GAAGGAGCAACAAGAGGAAG-3'(SEQ ID NO: 27). 29 cycles were performed at the following temperatures: 94° C. for 1 minute, 55 ° C. for 1 minute, and 72° C. for 1 minute. A sample of each reaction was then subjected to agarose gel electrophoresis.

Figure 3:
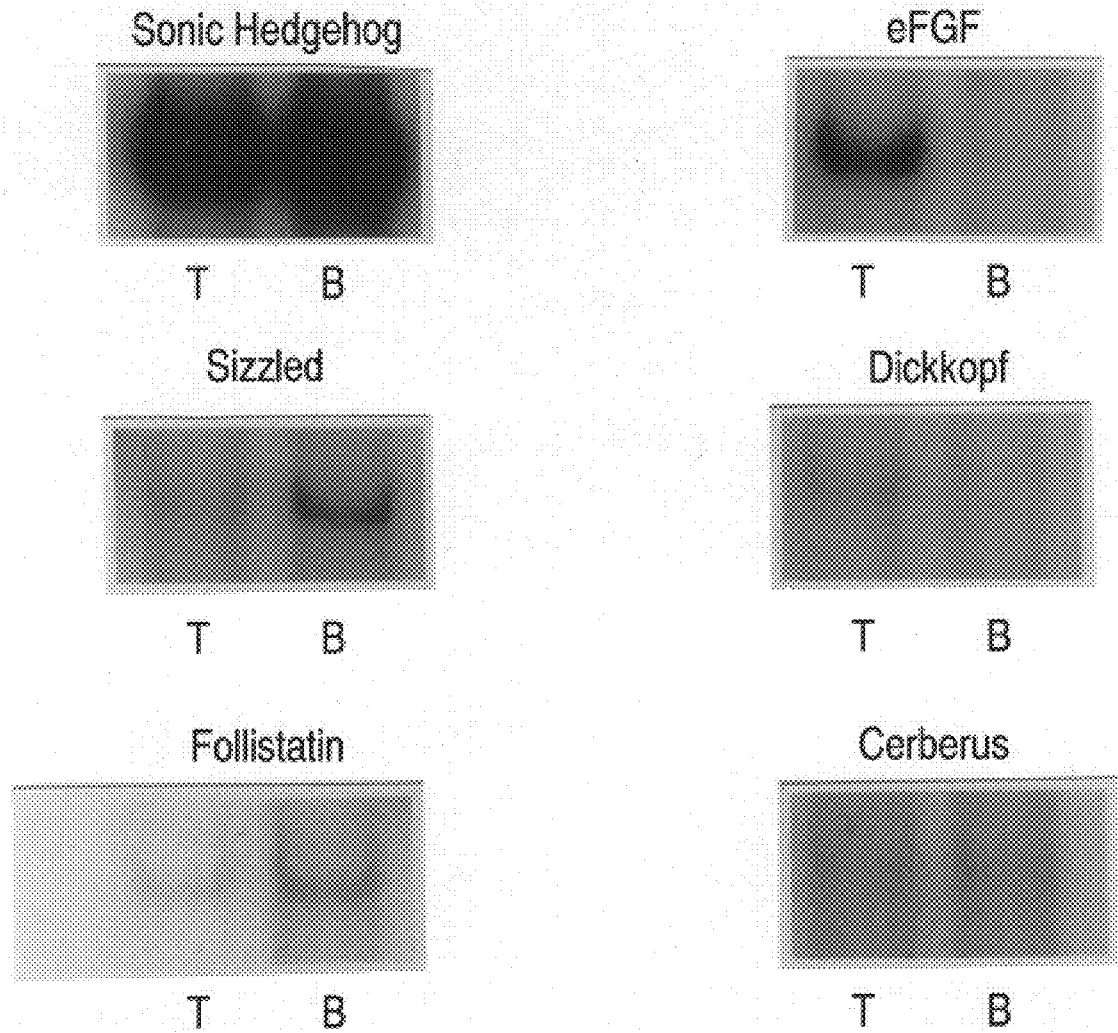
FIG. 3 shows photographs from agarose gels containing RT-PCR amplified RNA encoding secreted proteins isolated from the top ("T"), or bottom ("B") of a sucrose gradient loaded with a translation reaction containing microsomes and RNA generated from a Stage 11-15 Xenopus library.
Figure 4:
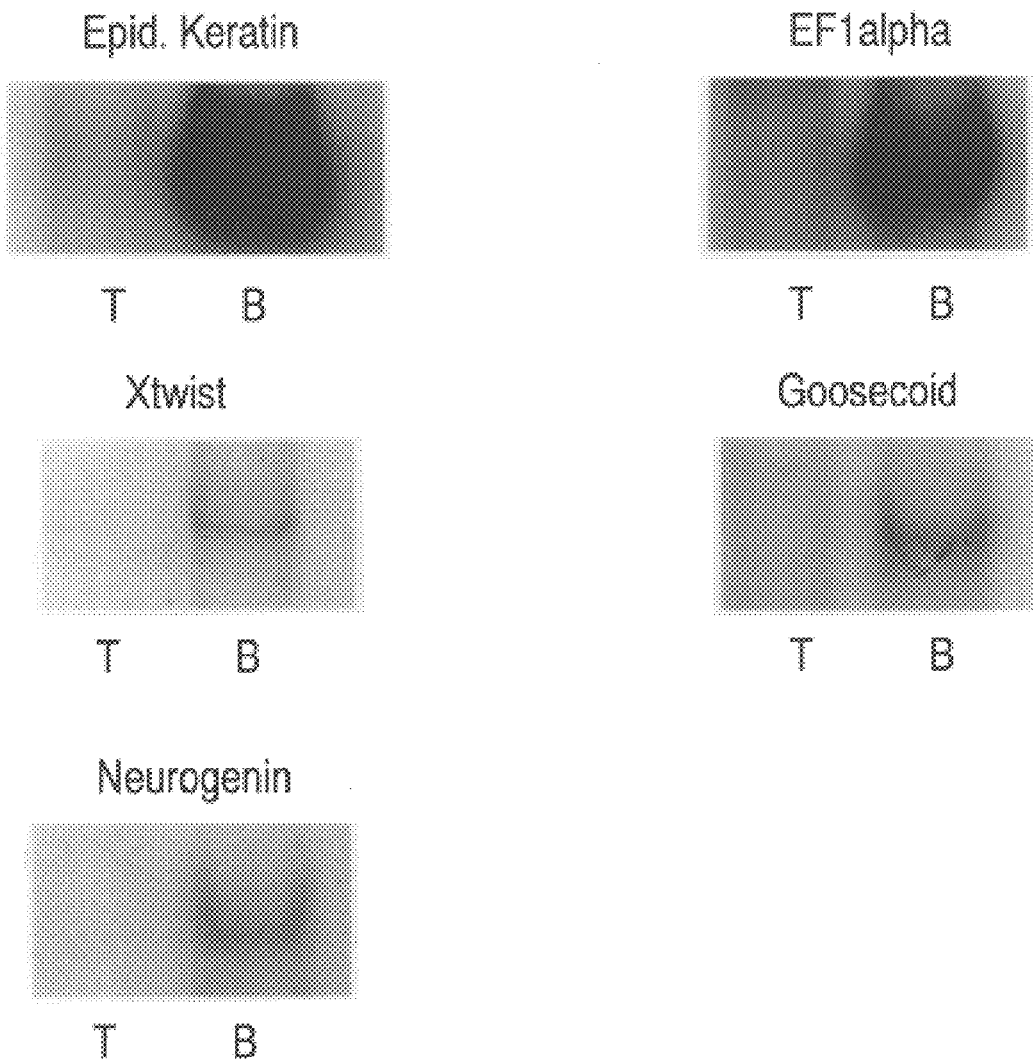
FIG. 4 shows photographs from agarose gels containing RT-PCR amplified RNA encoding cytosolic proteins isolated from the top ("T"), or bottom ("B") of a sucrose gradient loaded with a translation reaction containing microsomes and RNA generated from a Stage 11-15 Xenopus library.

FIGS. 3 and 4 shows PCR amplification products obtained using primers detecting secreted (FIG. 3) and cytosolic (FIG. 4) proteins, from RNA samples obtained from the top and from the bottom of the sucrose gradient. The results show that all the messages encoding secreted proteins that were tested were detected at the top of the gradient. The fact that the degree of floating varies somewhat for each message, probably reflects the efficiency of the translation machinery of the rabbit reticulocyte lysate, the processing of the translating proteins by the microsomal membranes, or both. Differences in the intensity of the signal between the different messages probably reflects the relative abundance of the messages in the library. FIG. 4 shows that, for messages encoding the non-secreted proteins that were tested, all were detected at the bottom of the gradient, but not at the top. Thus, RNAs encoding proteins which do not contain a signal peptide are never present at the top of the sucrose gradient. These results indicate that the method developed is able to select for RNAs encoding secreted proteins and that, more importantly, this method is able to select against those messages encoding cytoplasmic proteins. The results also show that this method can be generally applied to preexisting libraries, as shown for the staged Xenopus library.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A method for isolating a nucleic acid encoding a protein having a signal peptide, comprising isolating an RNA molecule associated with a microsome which is heterologous with respect to the RNA molecule under conditions wherein the RNA is at least partially translated.

2. The method of claim 1, wherein the protein having a signal peptide is a secreted protein.

3. The method of claim 1, further comprising synthesizing a single stranded DNA molecule from the RNA molecule.

4. The method of claim 1, wherein the RNA is from a mammalian cell.

5. The method of claim 1, wherein the RNA is translated in an in vitro translation system.

6. The method of claim 1, wherein the RNA which is at least partially translated is isolated from a cell or tissue sample.

7. The method of claim 3, further comprising converting the single stranded DNA molecule into a double stranded DNA molecule.

8. The method of claim 4, wherein the mammalian cell is a human cell.

9. The method of claim 5, wherein the in vitro translation system is a reticulocyte lysate.

10. The method of claim 5, wherein the RNA, the in vitro translation system and the microsomes are contacted, to thereby produce RNA which is partially translated and wherein RNA encoding a protein comprising a signal peptide is associated with the microsomes.

11. The method of claim 6, wherein the cell or tissue is a mammalian cell or tissue.

12. The method of claims 1, 3, or 7, further comprising inserting the RNA, the single stranded DNA molecule or the double stranded DNA molecule into a vector.

13. The method of claim 10, further comprising isolating the microsomes and the RNA associated therewith.

14. The method of claim 11, wherein the mammalian cell or tissue is a human cell or tissue.

15. The method of claim 12, wherein the vector is an expression vector.

16. A library of nucleic acids encoding proteins comprising a signal peptide, prepared according to the method of claim 12.

17. The method of claim 13, wherein the microsomes are isolated by sucrose density gradient centrifugation.

18. The library of claim 16, which is a cDNA library.

19. The library of claim 18, which is an expression library.

20. A method for isolating a nucleic acid encoding a protein having a signal peptide, comprising:

(i) contacting one or more RNA molecules with an in vitro translation system, to thereby produce one or more RNA molecules which are at least partially translated;

(ii) contacting the one or more RNA molecules which are at least partially translated with microsomes, such that the RNA molecules which are at least partially translated and which comprise a signal sequence associate with the microsomes, to thereby produce at least one RNA molecule associated with the microsomes;

(iii) isolating the microsomes and the at least one RNA molecule associated with the microsomes; and (iv) isolating at least one RNA molecule associated with the microsomes.

21. The method of claim 20, further comprising synthesizing a single stranded DNA molecule from the RNA molecule.

22. The method of claim 21, further comprising converting the single stranded DNA molecule into a double stranded DNA molecule.

23. The method of claim 22, further comprising inserting the double stranded DNA molecule into a vector.

24. The method of claim 23, wherein the vector is an expression vector.

25. The method of claim 24, further comprising producing a protein from the expression vector.

26. A method for preparing a library of nucleic acids enriched for sequences encoding secreted proteins, comprising (i) isolating RNA molecules associated with microsomes under condition wherein the RNA molecules are at least partially translated; and (ii) preparing an expression library with the isolated molecules.

27. A library of nucleic acids encoding proteins comprising a signal peptide, prepared according to the method of claim 26.

28. The library of claim 27, which is a cDNA library.

29. The library of claim 28, which is an expression library.

30. A method for enriching a population of RNA molecules in RNA molecules encoding a protein comprising a signal peptide, comprising (i) contacting a population of RNA molecules with a translation system, to thereby produce at least partially translated RNA molecules;

(ii) contacting the at least partially translated RNA molecules with microsomes under conditions in which the partially translated RNA molecules comprising a signal peptide associate with the microsomes;

(iii) isolating the microsomes and the RNA molecules associated with the microsomes; and (iv) isolating the RNA molecules from the microsomes, to thereby produce a population of RNA molecules enriched in RNA molecules encoding a protein comprising a signal peptide.

31. A method for preparing a double stranded nucleic acid encoding a protein having a signal peptide, comprising (i) isolating an RNA molecule associated with a microsome under conditions wherein the RNA is at least partially translated; and (ii) synthesizing a double stranded DNA from the at least partially translated RNA, to thereby obtain a double stranded nucleic acid encoding a protein having a signal peptide.

32. A method for identifying coding sequences for secreted polypeptides, comprising (i) isolating mRNA associated with microsomes to produce a library of mRNA enriched for coding sequences for polypeptides containing a signal peptide sequence;

(ii) cloning said library of mRNA into an expression vector to produce a library of expression vectors;

(iii) expressing the library of expression vectors to produce a library of polypeptides;

(iv) detecting the presence of secreted polypeptides in the library of polypeptides; and (v) identifying coding sequences from the library of expression vectors which encode the secreted polypeptides.

33. The method of claim 32, wherein the library of mRNA isolated form the microsomes is enriched for coding sequences for polypeptides containing a signal peptide sequence by a factor of at least 100 fold.

34. The method of claim 33, wherein the mRNA is from a source that is heterologous with respect to the source of microsomes.

* * * * *